(12) United States Patent
Pesach et al.

(10) Patent No.: US 12,727,965 B2
(45) Date of Patent: Sep. 8, 2026

(54) METHOD AND APPARATUS FOR DENTAL SURGICAL GUIDE VERIFICATION

(71) Applicant: LUMINX IL LTD, Hod HaSharon (IL)

(72) Inventors: Benny Pesach, Rosh Haayin (IL); Blanc Zach Lehr, Tel-Aviv (IL); Amitai Reuvenny, Kfar-Saba (IL)

(73) Assignee: LUMINX IL LTD

( * ) Notice: Subject to any disclaimer, the term of this patent is extended or adjusted under 35 U.S.C. 154(b) by 740 days.

(21) Appl. No.: 17/288,494

(22) PCT Filed: Oct. 23, 2019

(86) PCT No.: PCT/IL2019/051146

§ 371 (c)(1),
(2) Date: Apr. 23, 2021

(87) PCT Pub. No.: WO2020/084616

PCT Pub. Date: Apr. 30, 2020

(65) Prior Publication Data

US 2021/0386511 A1 Dec. 16, 2021

Related U.S. Application Data

(60) Provisional application No. 62/749,422, filed on Oct. 23, 2018.

(51) Int. Cl.
*A61C 1/08* (2006.01)
*A61B 6/03* (2006.01)
(Continued)

(52) U.S. Cl.
CPC .............. *A61C 1/082* (2013.01); *A61B 6/032* (2013.01); *A61B 6/51* (2024.01); *A61B 6/582* (2013.01); *A61C 19/04* (2013.01)

(58) Field of Classification Search
CPC ....... A61C 1/082; A61C 1/084; A61C 8/0089; A61C 8/009; A61B 17/176;
(Continued)

(56) References Cited

U.S. PATENT DOCUMENTS 5,320,462 A * 6/1994 Johansson ........... A61F 2/30942 356/601
5,562,448 A * 10/1996 Mushabac .......... A61C 13/0004 433/215
(Continued)

FOREIGN PATENT DOCUMENTS

EP 2 941 220 B1 11/2015
WO WO 2020/084616 4/2020

OTHER PUBLICATIONS

International Preliminary Report on Patentability Dated May 6, 2021 From the International Bureau of WIPO Re. Application No. PCT/IL2019/051146. (8 Pages).
(Continued)

*Primary Examiner* — Edelmira Bosques
*Assistant Examiner* — Holly T. To
(74) *Attorney, Agent, or Firm* — FENWICK & WEST LLP

(57) ABSTRACT

An in-vivo dental surgical guide verification method including: receiving first information including: dental surgical guide information of a dental surgical guide, and hard structure information of a hard structure of a patient's mouth; positioning the surgical guide within the patient's mouth; contacting a stylus to a surface of the hard structure of the patient mouth; acquiring image information corresponding to an image which includes at least a portion of the stylus and a portion of the dental surgical guide therein using an imager; and comparing the image information with the first information.

20 Claims, 15 Drawing Sheets

(51) Int. Cl.
*A61B 6/51* (2024.01)
*A61B 6/58* (2024.01)
*A61C 19/04* (2006.01)

(58) Field of Classification Search
CPC ....... A61B 17/1785; A61B 6/582; A61B 6/14; A61B 6/145; A61B 6/5241; A61B 34/10
See application file for complete search history.

(56) References Cited

U.S. PATENT DOCUMENTS

| | | | | |
|---|---|---|---|---|
| 6,000,939 | A * | 12/1999 | Ray | A61C 1/082 433/76 |
| 9,454,846 | B2 | 9/2016 | Pesach et al. | |
| 9,999,510 | B2 * | 6/2018 | de Clerck | A61C 13/00 |
| 11,813,132 | B2 * | 11/2023 | Pesach | A61B 1/00193 |
| 2005/0216024 | A1 * | 9/2005 | Massoud | A61B 17/176 606/87 |
| 2006/0105291 | A1 * | 5/2006 | Stein | B23B 47/28 433/75 |
| 2006/0240378 | A1 * | 10/2006 | Weinstein | A61B 17/17 433/76 |
| 2007/0037125 | A1 * | 2/2007 | Maev | A61B 8/0875 433/29 |
| 2009/0263764 | A1 * | 10/2009 | Berckmans, III | A61B 6/14 433/215 |
| 2010/0239996 | A1 * | 9/2010 | Ertl | A61C 19/043 433/29 |
| 2012/0021372 | A1 * | 1/2012 | Chen | A61C 1/084 433/29 |
| 2013/0273492 | A1 * | 10/2013 | Suttin, Sr. | A61C 8/0001 433/29 |
| 2013/0309628 | A1 * | 11/2013 | Orth | A61C 1/084 433/173 |
| 2014/0234803 | A1 * | 8/2014 | Hehn | A61C 9/0053 433/214 |
| 2015/0351866 | A1 * | 12/2015 | Thompson, Jr. | A61B 34/10 433/173 |
| 2015/0359479 | A1 * | 12/2015 | Crandall | A61B 6/12 433/29 |
| 2016/0338803 | A1 * | 11/2016 | Pesach | G06T 7/74 |
| 2016/0354169 | A1 * | 12/2016 | Suttin | A61B 17/3211 |
| 2019/0125297 | A1 * | 5/2019 | Chan | A61B 6/481 |
| 2019/0209267 | A1 * | 7/2019 | Massoels | A61C 1/082 |
| 2019/0343598 | A1 * | 11/2019 | Knobel | A61C 1/084 |
| 2023/0200935 | A1 * | 6/2023 | Ruehl | A61B 34/10 433/75 |
| 2023/0210631 | A1 * | 7/2023 | Geier | A61C 19/04 433/215 |

OTHER PUBLICATIONS

International Search Report and the Written Opinion Dated Feb. 4, 2020 From the International Searching Authority Re. Application No. PCT/IL2019/051146. (13 Pages).

Block et al. "Computed Tomography-Guided Surgery: Complications Associated With Scanning, Processing, Surgery, and Prosthetics", Journal of Oral and Maxillofacial Surgery, 67(11/Suppl.3): Nov. 13-22, 2009.

D'Souza et al. "Types of Implant Surgical Guides in Dentistry: A Review", Journal of Oral Implantology, 38(5): 643-652, Oct. 20, 2012.

Supplementary European Search Report and the European Search Opinion Dated Jul. 11, 2022 From the European Patent Office Re. Application No. 19875395.6. (8 Pages).

Communication Pursuant to Article 94(3) EPC Dated Dec. 23, 2024 From the European Patent Office Re. Application No. 19875395.6. (6 Pages).

* cited by examiner

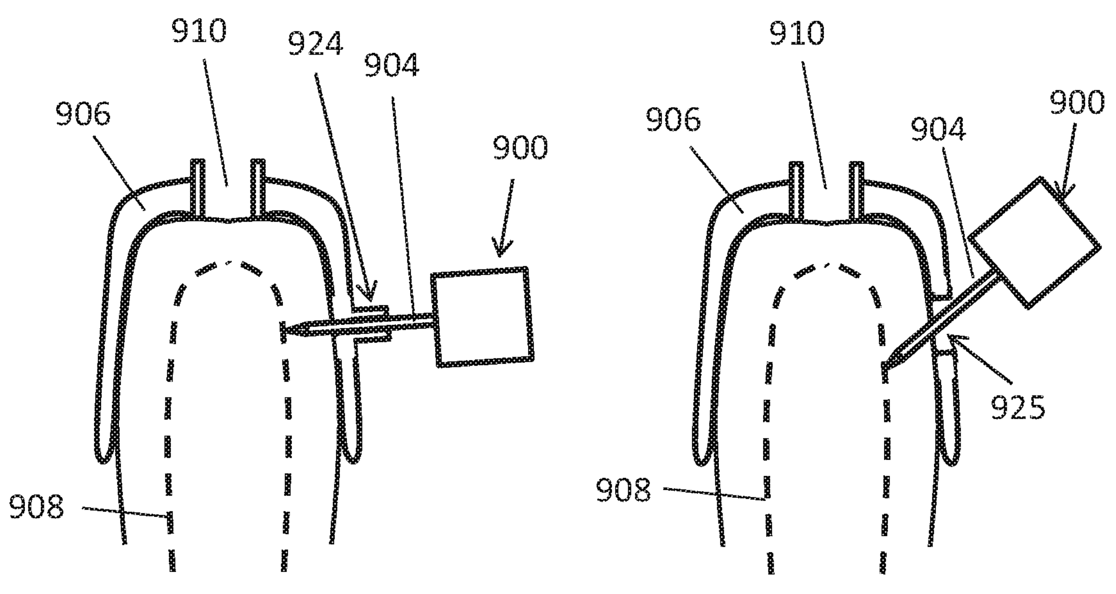
FIG. 9A
FIG. 9B
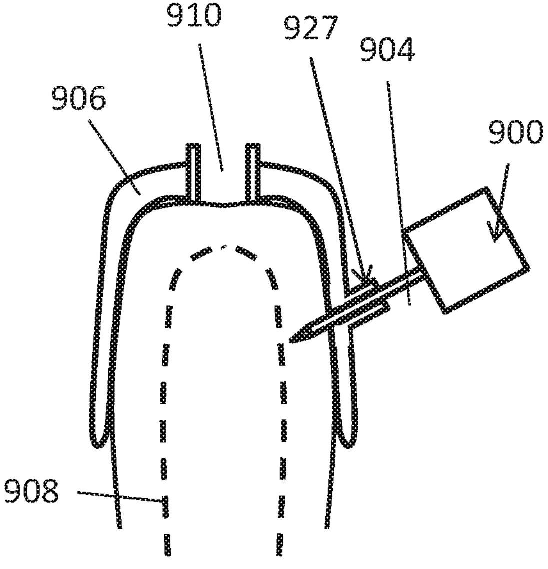
FIG. 9C

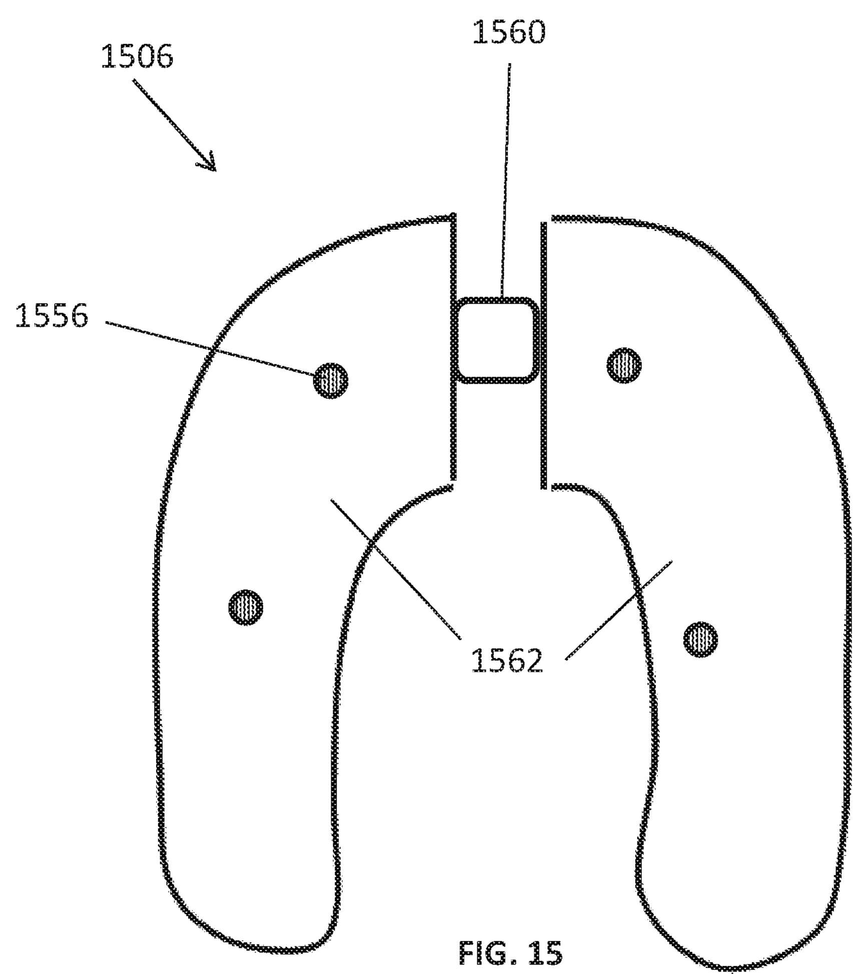
FIG. 15
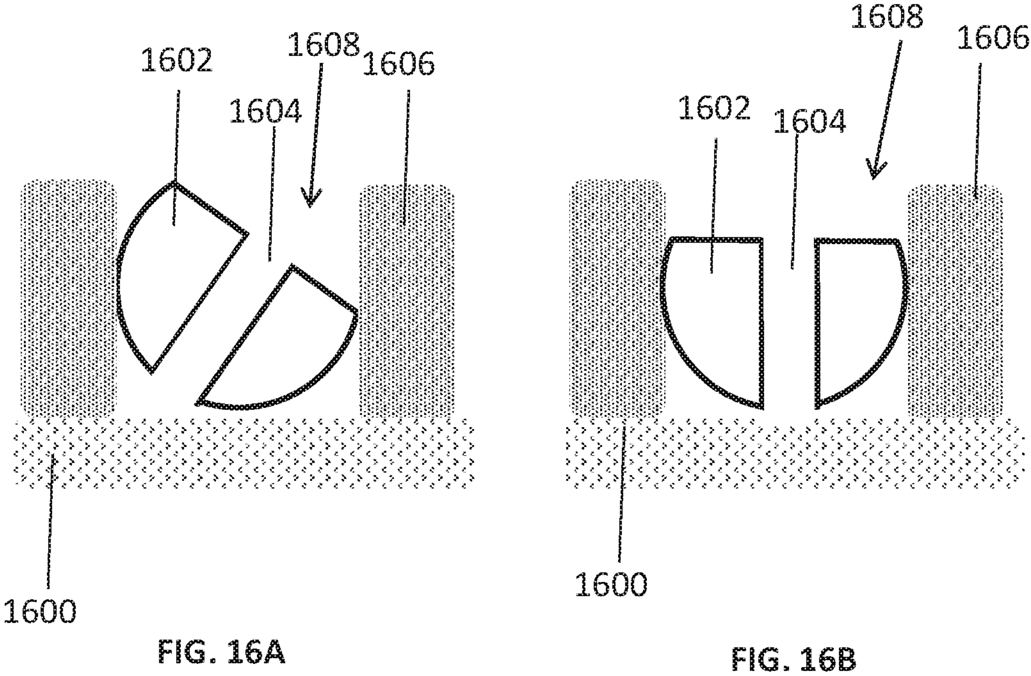
FIG. 16A
FIG. 16B

METHOD AND APPARATUS FOR DENTAL SURGICAL GUIDE VERIFICATION

RELATED APPLICATIONS

This application is National Phase of PCT Patent Application No. PCT/IL2019/051146 having International filing date of Oct. 23, 2019, which claims the benefit of priority under 35 USC § 119(e) of U.S. Provisional Patent Application No. 62/749,422, filed on Oct. 23, 2018.

The contents of the above applications are all incorporated by reference as if fully set forth herein in their entirety.

FIELD AND BACKGROUND OF THE DISCLOSURE

The present disclosure includes various inventions and associated embodiments thereof, including some embodiments relating to methods, systems, and devices for surgical guide verification and, more particularly, but not exclusively, to methods, systems, and devices for dental implant surgical guide verification.

Background art includes:

D'Souza et. al. "Types of Implant Surgical Guides in Dentistry: A Review", Journal of Oral Implantology, 2012

Block M S, Chandler C. Computed tomography-guided surgery: complications associated with scanning, processing, surgery, and prosthetics. J Oral Maxillofac Surg. 2009; 7:13-22

SUMMARY OF AT LEAST SOME EMBODIMENTS OF THE DISCLOSURE

Following are examples of some embodiments of the disclosure. Features of one example may be combined with features of one or more other examples, unless expressly prohibited and form additional examples of some embodiments of the disclosure.

Example 1. An in-vivo dental surgical guide verification method comprising:

receiving first information comprising:

dental surgical guide information of a dental surgical guide, and hard structure information of a hard structure of a patient's mouth;

positioning said surgical guide within said patient's mouth;

contacting a stylus to a surface of said hard structure of said patient mouth;

acquiring image information corresponding to an image which includes at least a portion of said stylus and a portion of said dental surgical guide therein using an imager; and comparing said image information with said first information.

Example 2. The method according to Example 1, wherein said first information includes a design model of said dental surgical guide.

Example 3. The method according to any one of Examples 1-2, wherein said hard structure includes measurement information of said patient mouth hard structure.

Example 4. The method according to Example 3, wherein said measurement information comprises CT measurement data.

Example 5. The method according to Example 1, wherein said first information includes a design model of said dental surgical guide and of said patient mouth hard structure.

Example 6. The method according to any one of Examples 1-5, wherein said comparing comprises:

estimating, using said image information, a first dimension between said dental surgical guide and said patient mouth hard structure; and comparing said first dimension with said first information.

Example 7. The method according to Example 6, wherein said estimating comprises:

estimating, using said image information:

a second dimension between said guide and said imager, said first dimension using:

said second dimension between said guide; and said imager and a third dimension between a tip of said stylus and said imager.

Example 8. The method according to any one of Examples 1-7, wherein said imager is calibrated to said stylus.

Example 9. The method according to any one of Examples 1-8, wherein said patient mouth hard structure is a patient bone structure.

Example 10. The method according to any one of Examples 1-9, wherein said contacting comprises inserting said stylus through at least one channel within said dental surgical guide.

Example 11. The method according to any one of Examples 1-10, further comprising generating feedback based on said comparing.

Example 12. The method according to Example 11, further comprising:

repositioning said dental surgical guide, within said patient's mouth, based on said feedback; and repeating said contacting, said acquiring and said comparing.

Example 13. The method according to Example 12, wherein said repositioning comprises adjusting at least one adjustor of said dental surgical guide.

Example 14. The method according to any one of Examples 11-13, further comprising:

adjusting a geometry of at least one portion of said dental surgical guide, based on said feedback; and repeating said contacting, said acquiring and said comparing.

Example 15. The method according to Example 10, wherein said at least one channel comprises a drill guide.

Example 16. The method according to Example 10, wherein said at least one channel comprises an anchoring pin channel.

Example 17. The method according to Example 10, wherein said at least one channel is sized and shaped to conform to and receive said stylus.

Example 18. The method according to any one of Examples 1-17, further comprising repeating said contacting and said acquiring for a plurality of points on said patient mouth hard structure.

Example 19. The method according to any one of Examples 1-18, wherein said stylus and said imager are operably connected.

Example 20. An in-vivo dental surgical guide verification method comprising:

receiving at least one design model corresponding to at least a hard mouth structure of a patient and a dental surgical guide;

positioning said surgical guide within a patient mouth;

contacting a stylus to a surface of said hard mouth structure;

acquiring an image including at least a portion of said stylus and a portion of said dental surgical guide using an imager;

generating a measurement model including said patient hard mouth structure and said dental surgical guide; and comparing said design model and said measurement model.

Example 21. The method of Example 20, further comprising generating feedback based on said comparing.

Example 22. The method of Example 21, further comprising displaying said feedback to a user through at least one user interface.

Example 23. An in-vivo dental surgical guide verification system comprising circuitry configured to:

receive at least one design model including a dental surgical guide and a mouth hard structure of a patient;

receive at least one image when a stylus is in contact with said mouth hard structure, said image including at least a portion of said stylus and at least a portion of said dental surgical guide;

estimate a dimension between said dental surgical guide and said patient mouth hard structure from said at least one image; and detect a mismatch between said image and said design model.

Example 24. The system according to Example 23, further comprising:

a dental measurement device including a distal portion sized and shaped to be inserted into a human mouth, said distal portion comprising:

said stylus; and at least one imager configured to acquire said at least one image.

Example 25. The system according to Example 24, wherein a field of view of said imager is configured to collect an image including at least one of said stylus and said dental surgical guide when said stylus is in contact with said mouth hard structure.

Example 26. The system according to any one of Example 23-25, wherein said stylus has a sharp tip.

Example 27. The system according to any one of Examples 23-26, wherein said stylus is rigid.

Example 28. The system according to any one of Examples 23-27, further comprising:

at least one contact sensor configured to measure contacts by said stylus; and circuitry configured to identify contact between said stylus and patient bone.

Example 29. An in-vivo dental surgical guide verification method comprising:

receiving a model of a patient hard mouth structure;

positioning said surgical guide in a position within a patient mouth, where the surgical guide includes one or more drill guide;

contacting a stylus to a surface of said hard mouth structure;

acquiring an image including said stylus and said dental surgical guide, using an imager;

estimating projected implant position with respect to said patient hard mouth structure, for said position, using said image and said model of said patient hard mouth structure.

Example 30. The method according to Example 29, comprising displaying to a user, said projected implant position with respect to said patient hard mouth structure.

Example 31. The method according to any one of Examples 29-30, comprising comparing said projected implant position to a design model; and generating feedback based on said comparing.

Example 32. The method according to Example 31, wherein said model includes one or more of a patient hard surface thickness surrounding said projected implant position, a proximity to a patient anatomical structure.

Unless otherwise defined, all technical and/or scientific terms used herein have the same meaning as commonly understood by one of ordinary skill in the art to which the present disclosure pertains. Although methods and materials similar or equivalent to those described herein can be used in the practice or testing of embodiments of the present disclosure, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present disclosure may be embodied as a system, method or computer program product. Accordingly, some embodiments of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of the method and/or system of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment of the present disclosure, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the present disclosure. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products according to embodiments of the present disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as collecting dental measurements, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the present disclosure are herein described, by way of example only, with reference to the accompanying drawings. With specific reference now to the drawings in detail, it is stressed that the particulars shown are by way of example and for purposes of illustrative discussion of embodiments of the present disclosure. In this regard, the description taken with the drawings makes apparent to those skilled in the art how embodiments of the present disclosure may be practiced.

In the drawings:

FIG. 9A is a simplified schematic cross-sectional view of a stylus contacting a bone surface through a stylus channel in a surgical guide, according to some embodiments of the present disclosure;

FIG. 9B. is a simplified schematic cross-sectional view of a stylus contacting a bone surface through a stylus channel in a surgical guide, according to some embodiments of the present disclosure;

FIG. 9C is a simplified schematic cross-sectional view of a stylus contacting a bone surface through a stylus channel in a surgical guide, according to some embodiments of the present disclosure;

FIG. 15 is a simplified schematic of an adjustable surgical guide, according to some embodiments of the present disclosure; and FIGS. 16A-B are simplified schematic cross sectional views of a drill guide within a channel of a surgical guide, according to some embodiments of the present disclosure.

ADDITIONAL DESCRIPTION OF AT LEAST SOME OF THE EMBODIMENTS

Figure 1A:
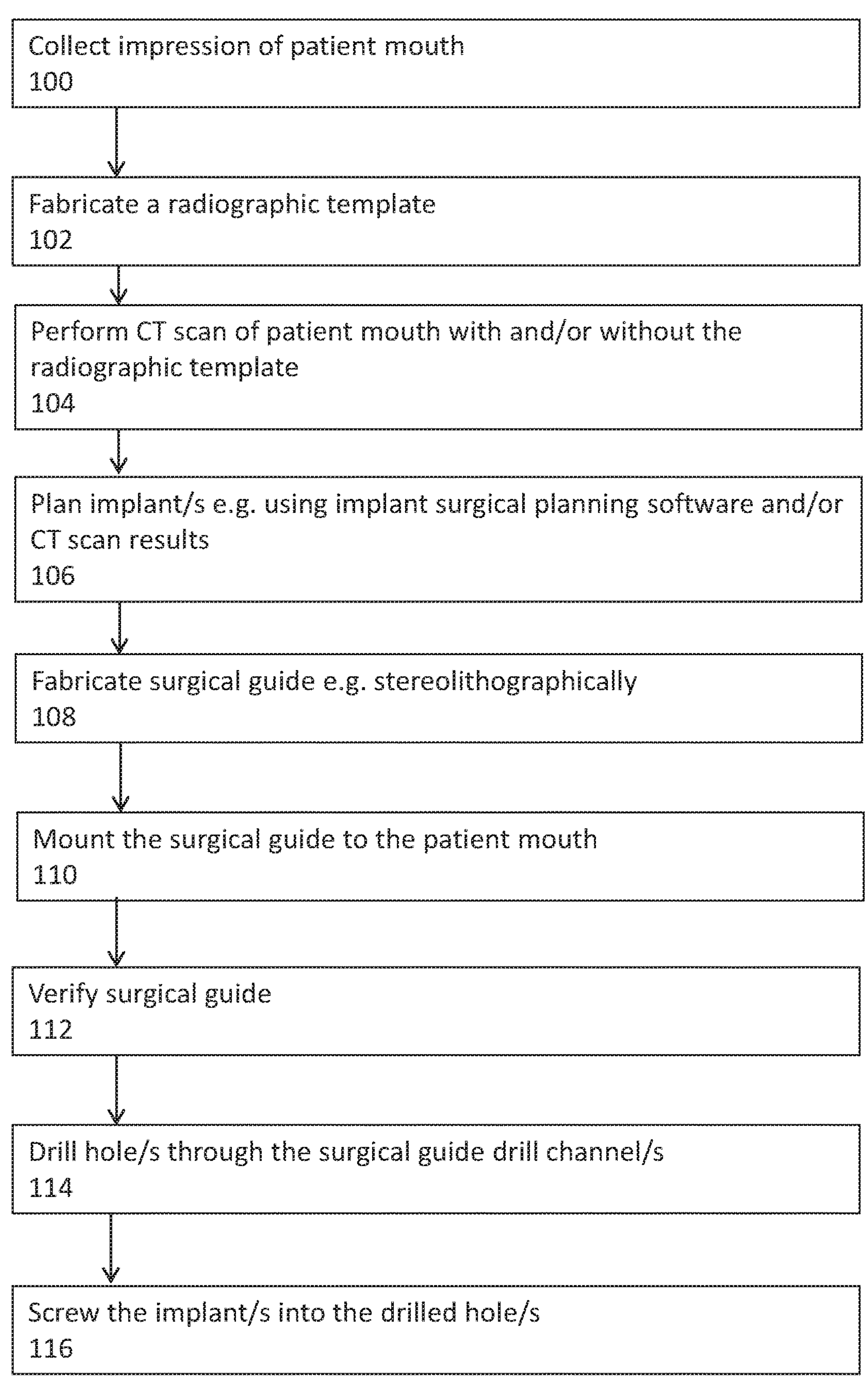
FIG. 1A is a flow chart of a method of placing dental implants, according to some embodiments of the present disclosure.

The present disclosure, in some embodiments thereof, relates to methods and devices for surgical guide verification and, more particularly, but not exclusively, to methods and devices for dental implant surgical guide verification.

Overview

A broad aspect of some embodiments of the present disclosure relates to verification of dental surgical guides, for example, dental implant surgical guides. In some embodiments, verification is with respect to underlying patient mouth surface/s, for example, hard surface/s e.g. one or more of bone, teeth, and preexisting prosthetic/s.

In some embodiments, verification is used to correct and/or optimize placement of the surgical guide within the patient's mouth. Alternatively or additionally, in some embodiments, verification is used to check topography of preplanned drilling sites to verify that planned drilling e.g. as defined by the surgical guide, is compatible with underlying mouth (e.g. bone) structures. Alternatively, or additionally, in some embodiments, verification is used to check geometry of the surgical guide, for example, that the right surgical guide is being used for the patient currently being treated and/or to check that the surgical guide has been accurately manufactured (e.g. according to a design model).

In some embodiments, verification is used in an iterative process where, for example, the surgical guide is repositioned to correct and/or optimize positioning of the surgical guide with respect to the bone structures and/or where geometry of one or more portion of the surgical guide is adjustable e.g. in some embodiments, position and/or orientation of drill guide channels are adjustable.

In some embodiments, adjustment includes adjustment of the surgical guide and/or of position of the guide is to enable use of a pre-existing prosthetic where verification shows that the prosthetic outcome is undesirable given the current surgical guide geometry and/or position.

In some embodiments, verification is of geometry of the surgical guide with respect to underlying patient mouth hard surface/s (e.g. bone), for example, verifying that hard patient surface/s have expected and/or appropriate geometry with respect to geometry of portion/s of the dental surgical device e.g. with respect to drill channels of the surgical guide. Where, in some embodiments, expected geometry is associated with model/s of one or more of: patient mouth structure/s, the surgical guide, drill path and/or implant path and/or final location with respect to one or more of the surgical guide and the patient mouth structure and model/s combining one or more of these features.

In some embodiments, verification includes verification of geometry of structures within the patient's mouth, given, for example, that bone structure (e.g. bone density) and/or mouth structure position (e.g. position of teeth) may change over time.

In some embodiments, verification of a surgical guide is in-vivo, for example, where the surgical guide is positioned (e.g. ready for use) within a patient's mouth. A potential advantage being the ability to verify the surgical guide without moving the patient.

In an exemplary embodiment, the surgical guide includes one or more drill guide for drilling associated with implant of dental implants. In some embodiments, verification includes verification of a position and/or orientation and/or size of a drill guide with respect to topography of the underlying bone structure e.g. along and/or adjacent to the drill path. Where, in some embodiments, a measurement is collected (e.g. of drill channel with respect to underlying bone structure) and analyzed to check that there are no issues with the projected drilled channel e.g. with bone thickness and/or impingement angle of the drill on the bone surface.

In some embodiments, a measured topography of the bone surface where the drill path impinges on the bone surface is verified e.g. that a structure (e.g. bone ridge) matches a model and/or conforms to one or more rule. In some embodiments, a projected resulting bone topography after drilling through the drill path is verified.

In some embodiments, drill holes are verified during a drilling process and/or after a drilling process is completed e.g. for one or all drill holes. For example, in some embodiments, a depth of a drill hole is verified (e.g. by collecting image/s while contacting a tip of a stylus to point/s within the drilled hole).

An aspect of some embodiments relates to verification of geometry and/or position of a dental surgical guide with respect to patient bone structure/s using measurement collected using a stylus and one or more imager.

In some embodiments, measurement includes using image/s acquired while a stylus is contacted to the hard surface (e.g. bone, tooth, prosthesis) where the image/s include the surgical guide and, optionally, the stylus. In some embodiments, one or more image includes both a portion of the stylus and a portion of the surgical guide. In some embodiments, one or more image includes a portion of the stylus or a portion of the surgical guide.

In some embodiments, geometry is estimated using the image/s and a known and/or a measured spatial relationship between imager/s collecting the images and the stylus. For example, in some embodiments, the stylus is pre-calibrated with the imager/s e.g. before measurements are collected. For example, in some embodiments, stylus position with respect to the imager is estimated from collected images.

In some embodiments, measurements (e.g. at discrete measurement points) are collected and are used to match and/or align the hard mouth surface and/or surgical guide with preexisting model/s.

In some embodiments, a plurality of measurements are collected. In some embodiments, the measurements are used to generate a measurement model (e.g. a 3D model e.g. including one or both of the hard mouth surface/s and the surgical guide). In some embodiments, the measurements are compared with a design model of the surgical guide and/or a previously collected measurements of patient hard structure/s. In some embodiments, the measurements are compared with a combined model of the surgical guide in position, with respect patient hard structures.

In some embodiments, the measurements are compared with a rule set and/or model including, for example, allowable ranges for one or more geometry parameter. Which, in some embodiments, enables validation without use of model/s of the surgical guide and/or patient bone structure. For example, where the rule set and/or model includes allowed angles of approach of drilling with respect to a bone surface.

In some embodiments, feedback is then generated based on the comparison. Where feedback, in some embodiments, includes one or more of verification of the surgical guide and/or positioning of the surgical guide, instructions to reposition the surgical guide, instructions to adjust the surgical guide (e.g. a geometry of the surgical guide e.g. a position and/or orientation of one or more drill guide), and an indication that the surgical guide is not suitable.

In some embodiments, feedback is used in manufacture of a new surgical guide, and/or an additional part to be attached to the surgical guide and/or patient mouth. In some embodiments, manufacture is on-site at the clinician (e.g. using CAM e.g. 3D printed), potentially reducing time required for fitting of prosthetic/s for the patient and/or clinician.

In some embodiments, the stylus is contacted to a hard patient surface (e.g. bone surface, tooth surface, prosthetic surface) through a channel in the dental guide. For example, through a drill guide (e.g. for an implant) of the dental guide. For example, through one or more anchoring channel/s, e.g. dedicated channel/s for stylus measurements.

In some embodiments, the stylus is contacted to a hard patient surface e.g. a tooth and/or existing prosthetic through an inspection window. Where, in some embodiments, the inspection window is sized and/or shaped to enable protrusion of the hard patient surface (e.g. tooth) to protrude, at least partially, from the surgical guide.

In some embodiments, a channel is made by the stylus, for example, the stylus being sufficiently hard and/or sharp to penetrate the surgical guide e.g. under manual force applied by a user. In some embodiments, the stylus is heated (e.g. using one or more heating elements thermally connected to the stylus) to a temperature at which material of the surgical guide (e.g. polymer material) softens sufficiently that the stylus may be inserted through the surgical guide e.g. under manual force applied by a user.

In some embodiments, measurements are collected from a plurality contact points accessed through a single channel. Alternatively or additionally, in some embodiments, measurements are collected through a plurality of channels in the dental guide. In some embodiments, one or more measurement is collected not through a channel in the surgical guide. For example, in some embodiments, measurement/s are collected at a periphery of the dental guide. For example, in some embodiments, the surgical guide partially covers the dental arch, and measurement/s are collected of hard mouth surface/s e.g. teeth and/or subgingival bone surface/s not covered and/or in a region of the surgical guide and/or surrounded by the surgical guide.

In some embodiments, measurements are collected through channel/s which are sized and/or shaped to accurately guide the stylus to a particular contact point. In some embodiments, measurements are collected through channel/s where the stylus has freedom of movement within the channel e.g. the stylus is smaller in (e.g. cross-sectional) size than the drill guide e.g. several measurements of different contact points are collected by inserting the stylus through a single channel in the surgical guide.

In some embodiments, a user collects measurements according to a measurement plan. In some embodiments, a measurement plan includes an order of channels to be measured and/or positions within channel/s to measure and/or number of measurements to collect. In some embodiments, a measurement plan is supplied with the surgical guide, for example, as user instructions and/or indication/s marked on the surgical device itself. Alternatively or additionally a measurement plan is provided, adjusted and/or generated by a system processor. In some embodiments, a measurement plan is communicated to a user through one or more user interface, e.g. using visual and/or audio guidance. In some embodiments, a measurement plan is adjusted, during measurement and/or during a treatment, based on collected measurements.

For example, in some embodiments, a measurement plan includes stylus measurements which are concentrated at a portion of interest of the bone structure e.g. portion/s of the bone structure proximal to an entrance point of the drill e.g. portion/s of the bone structure with highest curvature.

For example, in some embodiments, a user is directed (e.g. by user interface commands and/or feedback) in position and/or angle of insertion of the stylus. For example, in some embodiments, dedicated channels within the surgical guide for stylus insertion are directed to a region of interest. For example, in some embodiments, a drill guide insert includes one or more channel through which the stylus is inserted, where the insert is sized and/or shaped to control insertion direction of the stylus.

In some embodiments, a measurement plan includes collecting measurements from high curvature portion/s of bone structure meaning that, less contact measurements are required to align a pre-existing bone structure model/s with the measurement.

In some embodiments, the stylus and imager are connected to each other e.g. as parts of a dental measurement device: In some embodiments, the measurements are collected using a dental measurement device including one or more imager and a stylus.

Alternatively or additionally (where both kinds of stylus are used in collection of measurements), in some embodiments, a stylus and imager are not connected to each other, for example, a separate stylus being used e.g. in conjunction with an imaging device e.g. intraoral scanner (IOS) or even being used as an additional stylus in conjunction with a dental measurement device including an imager and a stylus. In some embodiments, the separate stylus includes one or more marking. In some embodiments, markings are used to identify a depth of insertion of the stylus e.g. with respect to the surgical guide e.g. depth is identified using one or more image including the stylus marking/s and the surgical guide. In some embodiments, markings are used to identify an orientation of insertion of the stylus, e.g. with respect to the surgical guide. In some embodiments, more than one stylus is used concurrently e.g. where a single image captures portion/s of more than one stylus where one or more of the plurality of styluses are in contact with the patient hard mouth structure and/or surgical guide.

In some embodiments, one or more anchoring pin is used as a stylus (e.g. alternatively or additionally to a stylus of a dental measurement device), where, in some embodiments, the anchoring pin includes markings (e.g. as described elsewhere in this document, e.g. regarding stylus markings) and/or includes one or more stop (e.g. as described elsewhere in this document e.g. regarding stylus stop/s). In some embodiments, image/s of an anchoring pin stylus are collected before, during and/or after positioning of the anchoring pin. In some embodiments, a stylus is contacted to an anchoring pin (e.g. through a channel in the surgical guide) to collect measurement/s. In some embodiments, a surgical guide is provided including one or more measurement pin including measurement marking/s. Where, in some embodiments, the pin/s are contacted to patient hard surface/s (e.g. and then imaged) to provide measurement/s.

Optionally, in some embodiments, the dental measurement device includes one or more projector configured to illuminate at least a portion of a FOV of the one or more imager. In some embodiments, illumination is with structured light. In some embodiments, the stylus is an elongated element which, in some embodiments, is orientated at an angle (e.g. 10-170°, or 40-140°, or 70-110°, or 80-100°, or about 90°, or lower or higher or intermediate ranges or angles) to a long axis of a body of the dental measurement device (where the device body, in some embodiments, is elongate). Where, in some embodiments, FOV of the imager includes at least a portion of the stylus.

In some embodiments, imager/s of the dental measurement device are operated with a sufficiently fast shutter speed so that images acquired by the imager/s do not have image smear associated with a hand-held device. For example, in some embodiments, shutter speed is 10 μs-200 ms, or 1 ms-50 ms, or 5 ms-20 ms, or less than 10 ms, or about 10 ms, or lower or higher or intermediate speeds or ranges.

Optionally, in some embodiments, the dental measurement device includes one or more sensor to detect contact (e.g. sufficient contact) between the stylus and bone. For example, one or more force sensor. For example, one or more stylus deflection sensor.

In some embodiments the stylus is sufficiently flexible that contact between the bone surface and the stylus is measured using measured deflection of the stylus. For example, in some embodiments, an image/s collected of the stylus are used to measure stylus deflection. For example, in some embodiments, one or more strain sensor e.g. disposed on the stylus is used to measure stylus deflection. For example, using one or more technique as described and/or illustrated in U.S. Pat. No. 9,454,846B2, incorporated here by reference in its entirety.

Alternatively, in some embodiments, the stylus is sufficiently rigid that force applied to the stylus to penetrate gum and contact bone does not deflect the stylus e.g. beyond a threshold value of deflection. In some embodiments, the stylus is sufficiently rigid and/or a tip of the stylus is sufficiently sharp that easily manually applied force (e.g. by a user) is able to penetrate the gums to contact bone. Whilst, in some embodiment a tip of the stylus is sufficiently blunt and/or has a widening stopper (e.g. has a portion wider than a cross-section of the stylus adjacent to the tip) that the force required for the stylus to penetrate the gums is not sufficient to pierce underlying bone.

In some embodiments, the stylus includes one or more stop e.g. a widening along a length of the stylus, which, for example, in some embodiments, prevents insertion of the stylus over a depth as defined by the stop. Alternatively or additionally, in some embodiments, a widening provides feedback to a user as to depth of insertion of the stylus (e.g. by increased difficulty of insertion at the widening).

In some embodiments, contact sensor and/or force sensor measurements are used to validate hardness and/or structural integrity of bone (e.g. a bone graft) selected to support an implant. Where, in some embodiments, a processor, identifying from measurement/s a lack in structural integrity of the bone, issues an alert (e.g. to a user through a user interface).

In some embodiments, the stylus has one or more sharp edge, for example, the sharp edge extending along a length of the stylus (e.g. parallel to the long axis) potentially enabling easy movement (e.g. cutting through gingiva) of the stylus along a hard mouth surface, e.g. after contact with the hard mouth surface.

An aspect of some embodiments of the present disclosure relates to a surgical guide.

In some embodiments, the surgical guide includes one or more marking e.g. fiducial marking. In some embodiments, fiducial markings include 2D marking/s. In some embodiments, fiducial markings include 3D markings. In some embodiments, image/s collected include the fiducial marking/s. In some embodiments, the stylus is contacted to a fiducial marking e.g. to calibrate the surgical guide in a coordinate space of the imager/s. In some embodiments, one or more channel (e.g. drill guide) includes one or more fiducial disposed around the channel. For example, where fiducials are sized and/or positioned on the surgical guide such that a dental measurement device imager field of view includes one or more portion of one or more fiducial when a stylus (e.g. a tip of the stylus) of the dental measurement device is positioned within the channel.

In some embodiments, a surgical guide includes more than one type of fiducial marking.

In some embodiments, a surgical guide includes opaque and/or reflective portion/s, for example, to increase contrast of the portion/s in images collected e.g. under illumination (e.g. illumination by structured light).

In some embodiments, the surgical guide includes one or more drill guide channel, for each implant. Additionally, in some embodiments, the surgical guide includes one or more anchoring pin channel. Additionally, in some embodiments, the surgical guide includes one or more additional measurement channel, to provide access to a stylus to patient tissue through the surgical guide.

In some embodiments, the surgical guide includes anchoring pins channels and/or additional measurement channels located on side walls of the surgical guide and/or interspersed between drill guide channels.

In some embodiments, the geometry of one or more portion of the surgical guide is adjustable e.g. in some embodiments, position and/or orientation of drill guide channels are adjustable. For example, in some embodiments, the surgical guide includes a plurality of rigid portions connected by adjustors, which in some embodiments.

Before explaining at least one embodiment of the present disclosure in detail, it is to be understood that the present disclosure is not necessarily limited in its application to the details of construction and the arrangement of the components and/or methods set forth in the following description and/or illustrated in the drawings and/or the Examples. Other embodiments of the present disclosure directed at one and/or another of inventions associated therewith, may be practiced or carried out in various ways.

Exemplary Methods

FIG. 1A is a flow chart of a method of placing dental implants, according to some embodiments of the present disclosure.

Optionally, at 100, impression of patient dental structures is made. For example, of the maxilla and/or mandibular e.g. with an inter arch index. In some embodiments, the impression is a physical impression. In some embodiments, the impression is a digital impression, for example, collected using an intra oral scanner (IOS) and/or other imaging technique/s e.g. CT.

Optionally, at 102, a radiographic template is fabricated, in some embodiments, using the impression. In some embodiments, the radiographic template is a replica of the desired prosthetic end result. Where, in some embodiments, the radiographic template and the impression (or patient's mouth) together illustrated the desired prosthetic end result. The template potentially allows a clinician to visualize the location of planned prosthesis/es (e.g. teeth e.g. implants) e.g. aesthetically and/or functionally and/or biomechanically. For example, in some embodiments, the visualization potentially assisting the clinician to plan and/or refine a planned location of the implant/s in the bone.

In some embodiments, an interocclusal index is fabricated, potentially facilitating reproducible placement of the radiographic template intraorally and/or potentially facilitating planning of the surgical guide.

At 104, in some embodiments, the patient's bone structures are imaged (e.g. by CT and/or other imaging modality/s e.g. MRI, ultrasound, intraoral scanner) with and/or without the radiographic template in position.

At 106, in some embodiments, implant surgical post and/or abutment positioning is planned. For example, using implant surgical planning software. Where, in some embodiments, the implant surgical planning software uses previously collected (e.g. at step 104) imaging data (e.g. CT imaging data).

In some embodiments, implant planning software enables observation of the arches and/or the radiographic scan template (e.g. simultaneously e.g. in 3 spatial planes). In some embodiments, the clinician views image data of bone morphology (e.g. using planning software) which potentially enables the surgeon to visualize the surgical bone site prior to implant placement, for example, enabling assessment of risks such as inadequate osseous support and/or compromise of important anatomic structure/s.

In some embodiments, planning is of one or more of location, angle, depth, and diameter of implant/s. In some embodiments, a commercially available implant planning software product is used. For example, SimPlant (Dentsply Sirona, York, USA), SurgiCase (Materialise Dental Inc, Leuven, Belgium), Procera (Nobel Biocare, Göteborg, Sweden), ImplantMaster (I-Dent Imaging Ltd, Hod Hasharon, Israel), coDiagnostiX (Straumann Holding AG, Basel, Switzerland), Easy Guide (Keystone Dental, Burlington, MA), Implant studio (3Shape A/S, Copenhagen, Denmark), and Romexis (Planmeca O Y, Helsinki, Finland).

At 108, in some embodiments, a surgical drill guide is fabricated (e.g. a stereolithographic guide. In some embodiments, the surgical guide includes one or more feature as described and/or illustrated regarding guide 406 FIG. 4.

In some embodiments, fabrication includes fabrication of a surgical sleeve placement e.g. including one or more feature of Straumann® Gonyx™ and Co Diagnostix™ system/s sleeve/s.

Optionally, in some embodiments, the surgical guide is verified (e.g. using one or more method and/or apparatus as described in this document) e.g. after manufacture e.g. at a site of manufacture. In some embodiments, the surgical guide is verified prior to positioning within (e.g. mounting to) the patient mouth (e.g. using one or more method and/or apparatus as described in this document).

In some embodiments, verification of the surgical guide (e.g. prior to positioning within the patient's mouth) includes measuring the surgical guide and inferring from the guide patient anatomy (e.g. which was previous used to plan the guide) which the clinician then compares with the patient anatomy before using the guide. In some embodiments, measurements (e.g. using one or more method and/or apparatus as described in this document) are used to build a model (e.g. a 3D model) of the surgical guide and/or patient anatomy which, in some embodiments, a processor compares with a design model of the surgical guide and/or a model of patient anatomy.

In some embodiments, verification of the surgical guide includes collecting images of the surgical guide including a reference, where, in some embodiments, the reference is marked on the surgical guide and/or is captured in image/s also including the surgical guide. In some embodiments, the reference includes fiducial marks and/or a ruler.

At 110, in some embodiments, the surgical guide is positioned within (e.g. mounted to) the patient mouth. For example, using one or more anchoring pin which passes through an anchoring channel in the surgical guide to contact and/or attach to patient bone. Alternatively or additionally mounting includes adhesive and/or clamping. In some embodiments, anchoring pin/s are adjusted with respect to the surgical guide and/or patient bone using one or more screw, for example a hexagon screw.

Figure 1B:
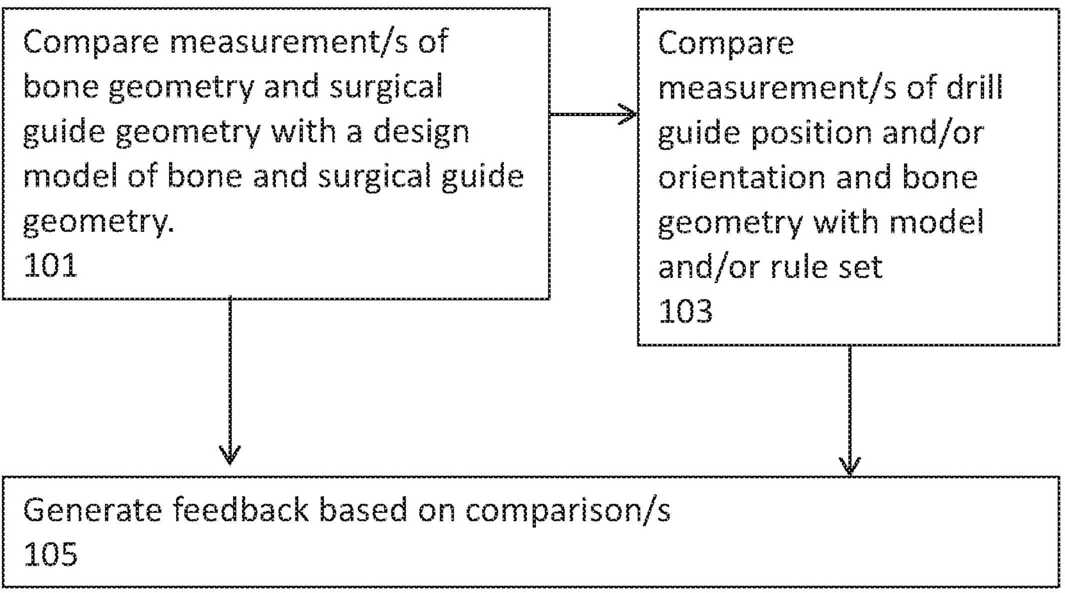
FIG. 1B is a flow chart of a method of surgical guide verification, according to some embodiments of the present disclosure.
Figure 2:
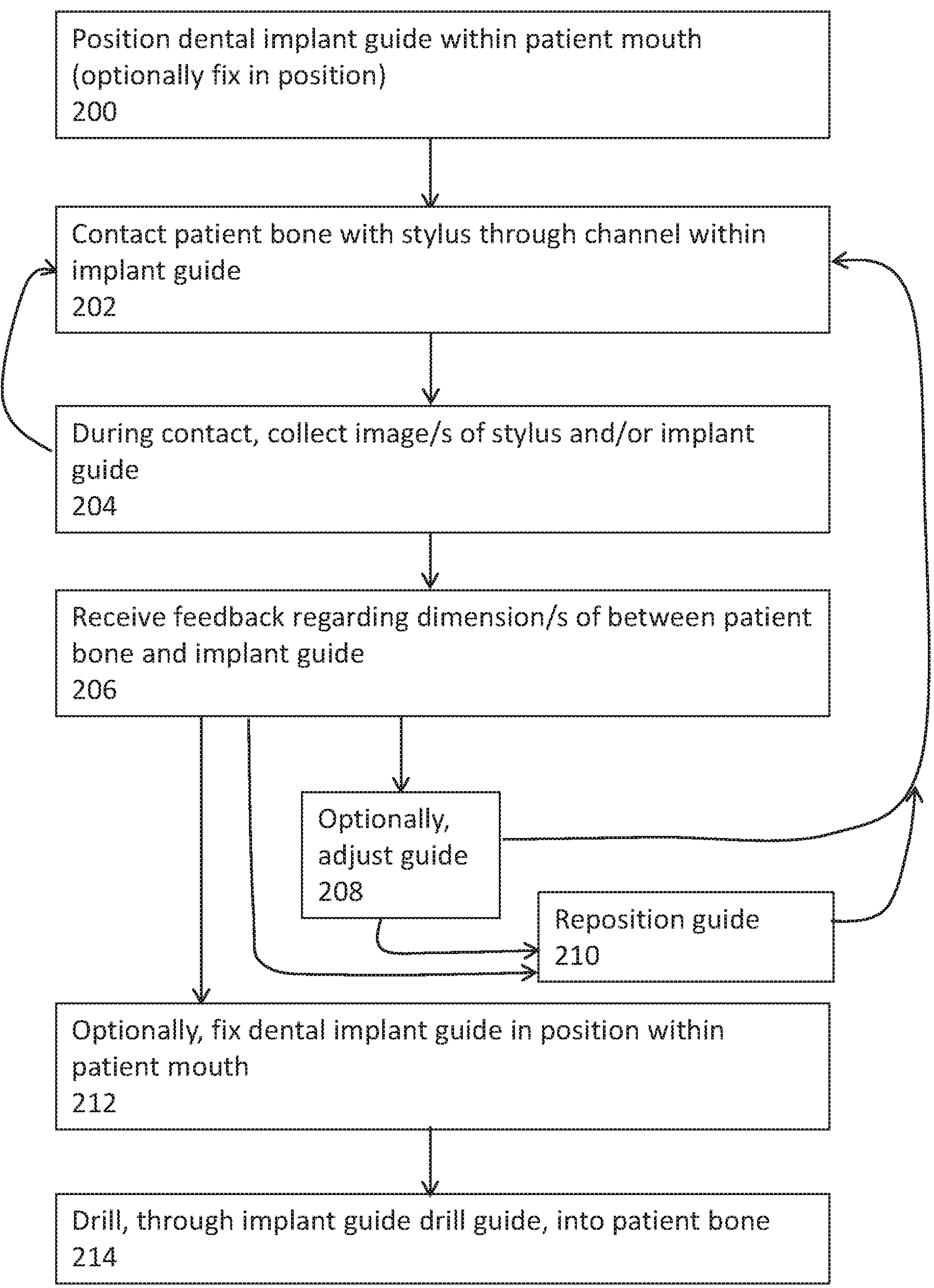
FIG. 2 is a flow chart of a method of in-vivo dental implant guide verification, according to some embodiments of the present disclosure.
Figure 3:
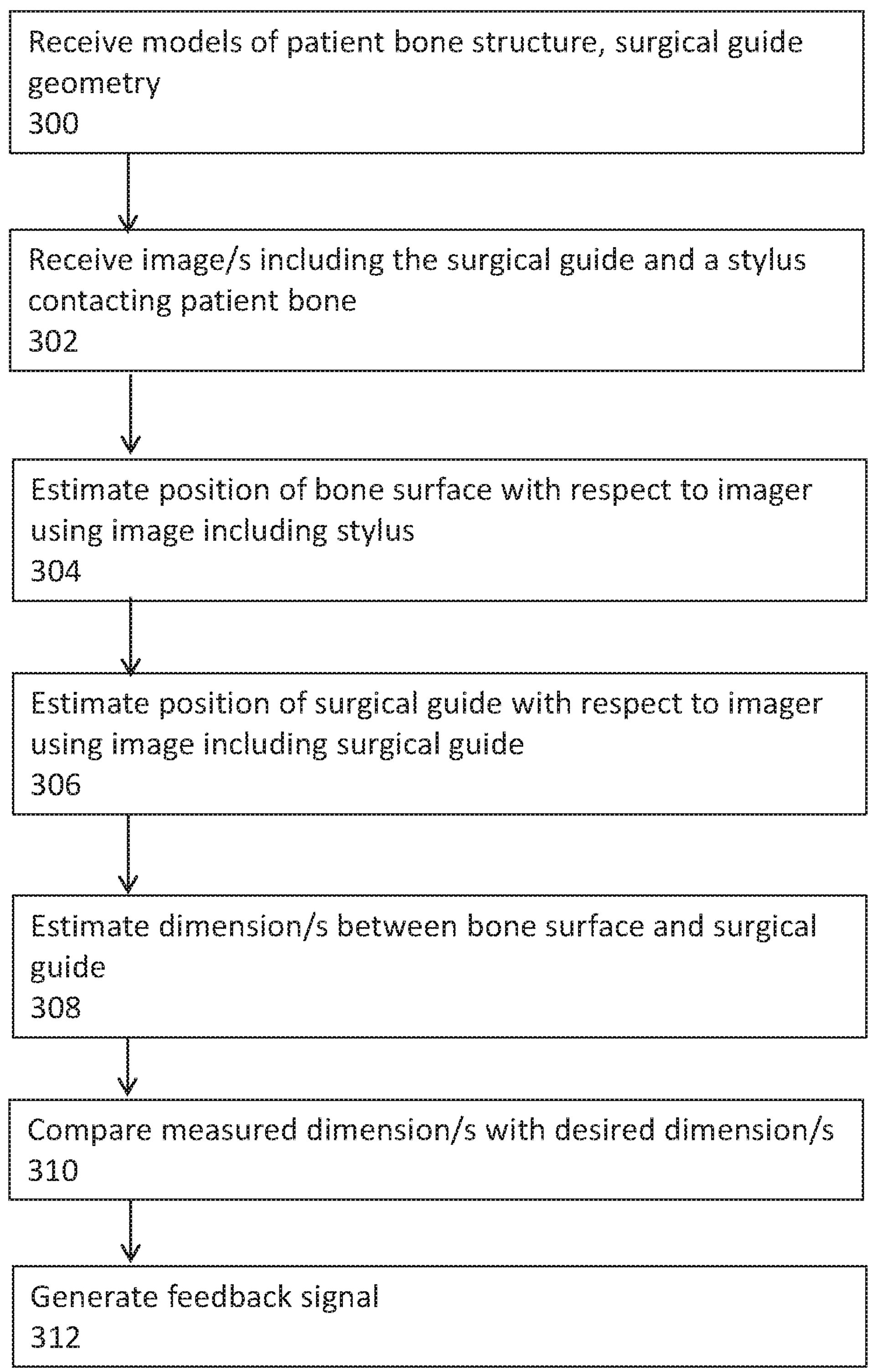
FIG. 3 is a flow chart of a method of dental implant guide verification, according to some embodiments of the present disclosure.

At 112, in some embodiments, the surgical guide is verified, e.g. including one or more feature as described regarding and/or illustrated in FIGS. 1B, 2, 3.

Potentially, verification of the surgical guide prevents use of an inaccurate guide and/or an inaccurately positioned guide. Where guide inaccuracy is, for example, due to inaccurate data collection and/or combining of data (e.g. impression and/or CT) and/or fabrication inaccuracies, and/or poor planning of implant position. Where the verification potentially reduces risk of mal-location of the implant/s and/or bone drilling causing one or more of nerve (e.g. mandibular nerve) damage, sinus penetration, penetration of maxillary and/or mandibular borders, and/or prostheses with aesthetic problems and/or implants and/or prostheses which are difficult to load into drill hole/s and/or prostheses which are difficult to attach to implant/s.

At 114, in some embodiments, one or more hole in drilled through the surgical guide (e.g. through drill guide channel/s) into patient tissue (e.g. gum and/or bone tissue).

At 116, in some embodiments, implant/s are positioned within (e.g. screwed into) the drilled hole/s, with or without the surgical guide in place (e.g. in some embodiments, the surgical guide provides guidance for insertion and/or attachment of implant/s into drilled channels.

FIG. 1B is a flow chart of a method of surgical guide verification, according to some embodiments of the present disclosure.

At 101, in some embodiments, measurement/s of bone geometry and surgical guide geometry are compared with a design model of bone and surgical guide geometry. Where, in some embodiments, the design model includes both the bone model and the surgical guide e.g. in a single 3D model.

At 103, alternatively or additionally, in some embodiments, position and/or orientation (topology) of a drill path (e.g. defined by surgical guide drill guide position and/or orientation) are estimated from measurement/s. In some embodiments, the topology of drill path/s are estimated with respect to a topology of underlying bone from measurement/s. In some embodiments, the drill path with respect bone is compared with a model and/or rule set.

At 105, in some embodiments, feedback is generated, based on the comparison/s.

FIG. 2 is a flow chart of a method of in-vivo dental implant guide verification, according to some embodiments of the present disclosure.

At 200, in some embodiments, a dental implant guide is positioned within a patient mouth. Where, in some embodiments, the dental implant guide includes one or more feature as illustrated and/or described regarding FIG. 4. In some embodiments, patient tissue is anesthetized and/or the patient is put under general anesthetic.

Optionally, in some embodiments, the dental implant guide is fixed into position within the patient's mouth. For example, using one or more anchoring pin and/or adhesive and/or clamping.

At 202, in some embodiments, a stylus is contacted to patient bone, for example, through a channel within the implant guide.

In some embodiments, the stylus is contacted to patient bone through a surgical flap cut within patient gum. In some embodiments, the gum lacks a flap (e.g. is flapless), the stylus being sufficiently sharp and/or rigid to penetrate the gums, e.g. under force easily applied manually by a clinician. In some embodiments, the stylus includes a blade configured for cutting a flap in the gum.

In some embodiments, a tip of the stylus contacting the bone is not visible, for example, being covered by gums and/or (e.g. in the case of contact through the gums (e.g. through a flap in the gums)) blood and/or other fluid and/or tissue.

In some embodiments, the channel is a drill guide for a dental implant. In some embodiments, the channel is an additional channel through the surgical guide. In some embodiments, the stylus is contacted through gum at a periphery of the surgical guide (e.g. outside the surgical guide and not through a channel in the surgical guide).

Optionally, in some embodiments, contact with the bone surface and/or other hard mouth object/s (e.g. teeth and/or existing dental prosthetic/s), is verified e.g. by sensor signal/s.

Optionally, in some embodiments, the stylus is contacted to a surface of the surgical guide, for example, to one or more guide fiducial.

At 204, in some embodiments, during contact of the stylus (e.g. with patient bone) image/s are collected. In some embodiments, one or more image includes a portion of the stylus and/or a portion of the implant guide. In some embodiments, the surgical guide and/or stylus includes one or more fiducial marker and one or more image includes the fiducial/s. In some embodiments, during collection of image/s, the area being measured is illuminated e.g. with structured light.

In some embodiments, images are 3D images, e.g. collected using 3D imager/s. In some embodiments, 2D images are collected.

In some embodiments, steps 202 and 204 are repeated. For example, for multiple contact points through a single channel in the surgical guide and/or for a plurality of channels within the surgical guide. In some embodiments, step 204 is repeated as the stylus tip remains in contact, as an angle of insertion of the stylus is changed, potentially providing images including different portions of the surgical guide.

In some embodiments, steps 202 and 204 are repeated for at least two channels within the surgical guide (where, in some embodiments, the at least two channels are both drill guides). Where, in some embodiments, for each channel, a plurality of measurements at different stylus contact points are collected. In some embodiments, to verify the surgical guide in 6 degrees of freedom (DOF) a minimum of contact points between the stylus and bone is 4 points, none of which are co-planar.

In some embodiments, at least one measurement is collected from every drill guide tube in the surgical guide. For example, to verify that each tube is correctly positioned and/or orientated e.g. with respect to the underlying bone.

In some embodiments, a minimum number of channels are measured. Where, in some embodiments, the minimum number is per surgical guide. For example, 2-30, or 2-20, or 2-10, lower or higher or intermediate numbers of channels. In some embodiments, the minimum number is per area of the surgical guide. Where, in some embodiments, different portions of the surgical guide have different minimum number of guides. For example, a region of the surgical guide including a drill channel, in some embodiments, has a higher minimum number of measurement channels than a region lacking a drill channel. In some embodiments, a minimum number of channels is affected by number and/or topography of other mouth hard surfaces (e.g. teeth) by which the surgical guide is supported, optionally with respect to drill channel/s.

In some embodiments, validation is of geometric parameter/s of the surgical guide. For example, in some embodiments, validation includes measurement of size (e.g. diameter) of one or more drill guide. Where, in some embodiments, feedback provided to a user includes a drill specification, e.g. based on the drill guide measurement/s.

In some embodiments, validation is of positioning and/or orientation of the drill guide. In some embodiments, one or more drill guide is repositioned, where in some embodiments, repositioning includes removing and inserting the drill guide into the surgical guide e.g. before and/or during treatment using the surgical guide.

In some embodiments, validation is performed repetitively during a treatment. For example, to verify the surgical guide position and/or drill guide position and/or orientation after treatment which potentially moves and/or distorts the surgical guide.

In some embodiments, validation is performed before and after anchoring pin attachment. For example, to verify that the process of anchoring pin attachment does not dis-align and/or distort the surgical guide topography and/or or bone topography.

In some embodiments, validation is performed during drilling. For example, to validate that drilling has not moved (e.g. translated and/or twisted) the surgical guide. For example, where an implant hole is drilled and then enlarged, e.g. the enlargement being performed with a different drill bit. In some embodiments, enlargement and/or drilling is performed using the implant itself e.g. as a drill bit, for example using a BLX Straumann implant. In some embodiments, the implant hole is measured e.g. with respect to surrounding bone structure, using the stylus, before enlargement of the implant hole. For example, to verify that a wider hole will not over-thin and/or breach surrounding bone structure/s.

In some embodiments, validation is performed after removal of gingiva (e.g. by punching).

At 206, in some embodiments, feedback regarding geometries of the patient's bone and the implant guide, for example, with respect to expected geometries, is received e.g. by a user. For example, in some embodiments, feedback is communicated to a user through one or more user interface.

Optionally, at 208, in some embodiments, (for example, if feedback received indicates that the surgical guide is not verified) the surgical guide is adjusted, optionally, based on the received feedback. For example, a user receives instructions, based on the feedback, as to how to adjust the surgical guide.

In some embodiments, adjustment includes position and/or orientation of one or more drill guide.

In some embodiments, adjustment includes adjusting one or more adjustor. In some embodiments, feedback received by a user includes instructions as to how much to adjust one or more adjustor (e.g. adjustor 1356 in FIGS. 13A-B, 1456, 1457 in FIG. 14).

In some embodiments, steps 202, and 204 are then repeated.

In some embodiments, feedback includes communication of measurement/s to a user. For example, in some embodiments, measurements are used to generate a projected model (e.g. 3D model) of patient bone structure/s including projected position of implants and/or prosthesis/es e.g. as estimated from measurements. In some embodiments, the model is displayed, optionally, along with a design model including the patient bone structure/s and planned position of implants.

Optionally, at 210, in some embodiments, if feedback received indicates that the surgical guide is not verified, the surgical guide is repositioned within the patient's mouth, optionally based on the received feedback. For example, in some embodiments, a user applies pressure to one or more portion of the surgical guide (and/or "wiggles" the guide) e.g. to more closely fit the guide to the patient/s mouth.

In some embodiments, feedback includes a reason for misplacement and/or instructions as to repositioning. For example, in some embodiments, feedback indicates that the surgical guide is not placed over one tooth accurately and/or an anchoring pin is not attached to patient bone correctly.

In some embodiments, the surgical guide position is adjusted relative to anchoring pin/s. For example, in some embodiments, an orientation of the surgical guide is adjusted rotating the surgical guide around an anchoring pin. In some embodiments, a distance between the surgical guide and underlying bone is adjusted e.g. using one or more feature as illustrated in and/or described regarding FIGS. 12A-B and/or FIGS. 13A-B and/or FIG. 14 and/or FIG. 15.

In some embodiments, steps 202, and 204 are then repeated.

Optionally, at 212, in some embodiments, if feedback received indicates that the surgical guide is verified, the surgical guide is fixed in position within the patient's mouth, for example, using one or more technique as described regarding step 200.

At 214, drilling into patient bone is commenced through one or more guide drill guide.

FIG. 3 is a flow chart of a method of dental implant guide verification, according to some embodiments of the present disclosure.

At 300, in some embodiments, a patient model is received, which includes, for example, hard patient structure/s (e.g. a patient bone structure model). In some embodiments, the model includes jaw bone/s and optionally teeth and/or existing dental prosthetic/s.

In some embodiments, a model of a surgical guide geometry is received. In some embodiments, one or more model is received from planning software (e.g. implant surgical planning software and/or surgical guide design software) for example, including one or more feature as described regarding step 106 FIG. 1A.

In some embodiments, the patient and/or surgical guide mode are 3D models. Alternatively or additionally, in some embodiments, the patient and/or surgical guide model includes dimensions and/or landmarks.

In some embodiments, the model/s received include a desired spatial relationship between the patient model and the surgical guide model, modeling the surgical guide in place in the patient's mouth, e.g. prior to and/or during treatment.

At 302, in some embodiments, image/s (e.g. 2D and/or 3D images) including at least a portion of the surgical guide (and, optionally, at least a portion of a stylus) where the stylus is contacting patient bone (e.g. a tip of the stylus is contacting patient bone) are received.

At 304, in some embodiments, a position of the bone surface with respect to the imager is estimated. For example, by estimating a spatial relationship between a portion of the stylus captured in the image and the imager, and inferring from this spatial relationship, a spatial relationship between the stylus tip and the imager. For example, using stylus calibration to the imager where, for example, in some embodiments, a position of a tip of the stylus is known with respect to the imager.

At 306, in some embodiments, a position of a portion of the surgical guide with respect to the imager is estimated, using the collected image/s.

In some embodiments, where a 3D model of the surgical guide is known, and where a plurality of features (e.g. channel opening/s, fiducial/s) on the surgical guide are identified from 2D images, a location of the surgical guide with respect to the imager is estimated from the 2D images. In some embodiments, a model (e.g. 3D model) of the surgical guide includes position and/or nature of fiducials (e.g. 2D and/or 3D fiducials) of the surgical guide.

For example, if intrinsic parameters of a 2D imager are known, and the 3D model of the surgical guide is known, the 3D location and rotation of the 2D imager can be found e.g. using one or more of Structure From Motion (SFM), 2D Simultaneous Localization And Mapping (SLAM) algorithms.

Where, in some embodiments, intrinsic parameters of an imager include one or more of imager focal length, image sensor format, skew, and principal point. In some embodiments, intrinsic parameters includes nonlinear intrinsic parameter/s, for example, lens distortion. In some embodiments, one or more imager parameter is found by calibrating the imager, which, in some embodiments, includes nonlinear optimization technique/s e.g. bundle adjustment.

In some embodiments, using the 3D location of and rotation (e.g. in 6DOF) of the imager, a stylus tip location relative to the surgical guide can be estimated, e.g. as described elsewhere in this document.

At 308, using position of the bone surface (step 302) and surgical guide (step 306) with respect to the imager, dimension/s between the bone surface and surgical guide are estimated. In some embodiments, a model (e.g. 3D model) of the bone structure and/or guide and/or a space therebetween is generated from the images.

In some embodiments, measurements are used to estimate orientation and/or position of a drill guide channel with respect to underlying patient bone, for example in 6DOF. In some embodiments, a drill guide upper rim is identified from image/s and the position of the upper rim of the drill guide is measured with respect to the bone structures. In some embodiments, orientation and/or position is estimated in 5DOF, since rotation through the tube axis may be invariant for the drill.

In some embodiments, estimation is of at least a portion of a drill path through patient bone (e.g. defined by surgical guide drill guide position and/or orientation). In some embodiments, the topology of drill path/s are estimated with respect to a topology of underlying bone from measurement/s. In some embodiments, the drill path with respect to bone is compared with a model and/or rule set.

At 310, in some embodiments, measurement dimension/s and/or measurement model/s are compared with desired dimension/s and/or a desired model (e.g. a design model). In some embodiments, comparison is with a rule set. For example, where, in some embodiments, rule/s include one or more of; an allowable range for angle of approach of a drill path with respect to a bone surface, an allowable range of estimated bone thicknesses surrounding a drill hole into the bone after drilling along the drill path, a distance of the drill hole from one or more patient anatomical structure, for example from a nerve (e.g. mandibular nerve), a sinus, a maxillary border, a mandibular border.

At 312, in some embodiments, a feedback signal is generated, based on the comparison. For example, in some embodiments, the signal indicates that the surgical guide is verified and that drilling and/or fixing of the surgical guide in place may proceed. For example, in some embodiments, if the error in position and/or geometry of the surgical guide is too high, a feedback warning and/or instructions as to how a user should proceed are generated.

For example, in some embodiments, feedback includes an estimated projected a minimal bone wall thickness around the drill along the drill path, where in some embodiments, the minimum thickness is communicated to a user. In some embodiments, the estimated projected thickness is compared with a threshold (which, in some embodiments, is different depending on the implant and/or prosthesis type and/or bone density of the patient) and, in some embodiments, if the thickness is smaller than the threshold an alert and/or error message is communicated to the user. For example, the thickness is shown on a display in red text.

Exemplary Surgical Guide

Figure 4:
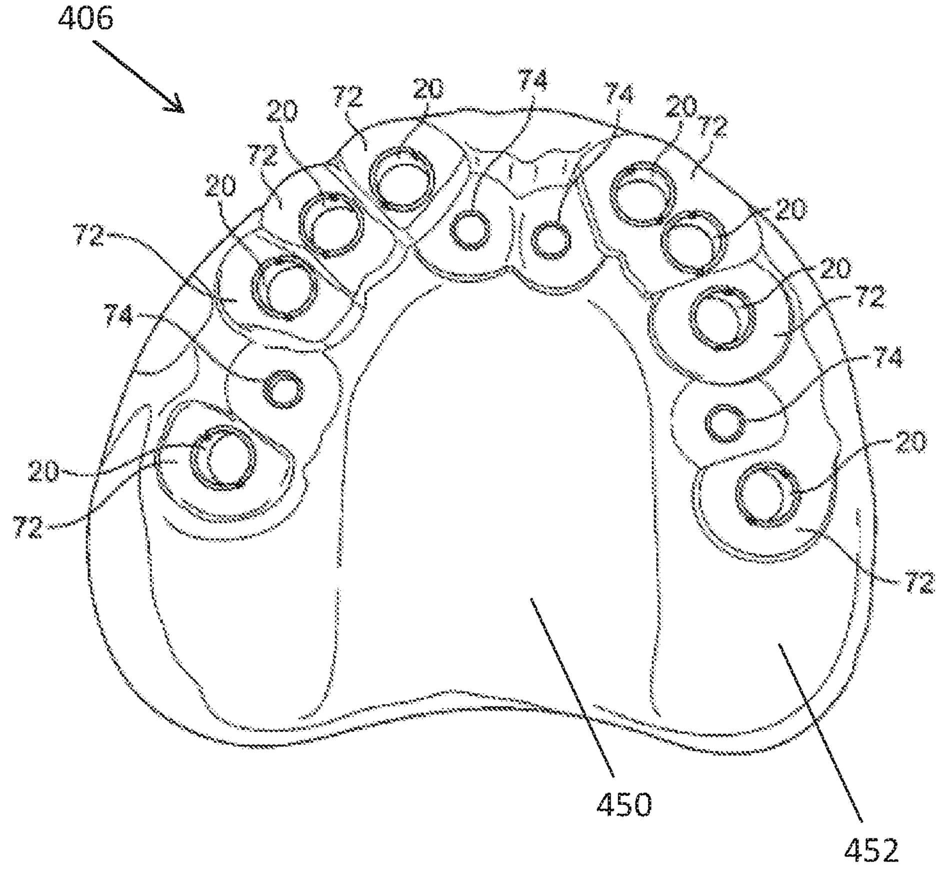
FIG. 4 is a simplified schematic of a dental implant guide, according to some embodiments of the present disclosure.

FIG. 4 is a simplified schematic of a dental implant guide 406, according to some embodiments of the present disclosure.

In some embodiments, guide 406 includes one or more channel e.g. a plurality of channels 20, 72, 74. In some embodiments, the surgical guide includes a portion 450 extending to fit to and/or cover a patient/s palate (e.g. hard and/or soft) and/or configured to cover and/or be disposed underneath the patient's tongue.

Alternatively, in some embodiments, 450 is patient tissue.

In some embodiments, the plurality of channels include different sized channels e.g. for different sized implants e.g. where a portion of the channels are implant drill guides and a portion have another purpose e.g. for anchoring pins e.g. to provide access to the stylus.

In some embodiments, guide 406 is shaped to fit closely to patient jaw hard and/or soft surfaces e.g. teeth, pre-existing dental prosthetic/s, gum topology.

In some embodiments, the surgical guide includes a shaped polymer portion 452, which in some embodiments is transparent.

In some embodiments, the polymer portion includes one or more channel 20, 72, 74 configured to receive a drill guiding tube where drill guiding tube/s include, in some embodiments, stainless steel and/or titanium. In some embodiments, the drill guiding tube/s are sized and/or shaped to guide osteotomy drill/s potentially precluding the need for pilot drills.

In some embodiments, the surgical guide is custom fabricated for a particular patient, for example, using imaging data of patient anatomy (e.g. of hard patient structure/s e.g. bone). In some embodiments, the surgical guide is adjustable, for example, including one or more adjustable part. Where, in some embodiments, adjustment is in response to feedback based on measurements. For example, in some embodiments, positon and/or angle of guiding tube/s are adjustable. For example, in some embodiments, the surgical guide includes one or more rail and one or more drill guiding tube is mounted to a rail and positionable at more than one location on the rail. For example, in some embodiments, a drill guide is removed and reinserted into the surgical guide e.g. to correct an angle of the drill guide with respect to and/or depth of insertion of the drill guide into the surgical guide.

In some embodiments, a surgical guide includes removable drill guides and/or is provided lacking one or drill guide. Where, in some embodiments, a drill guide is selected and inserted and/or replaced e.g. based on collected measurements. For example, in some embodiments, a surgical guide is provided as part of a kit including separate drill guides for insertion at the treatment site (e.g. in vivo) and/or for replacement.

In some embodiments, a surgical guide follows a contour of a jaw e.g. covering teeth and/or gum surface/s of the entire jaw.

In some embodiments, the surgical guide partially covers a jaw e.g. covering a contour of a portion of the jaw. Where, in some embodiments, measurements include measurement of hard patient surface/s e.g. teeth, bone, which are not in contact with and/or have a circumference which is partially (or not at all) contacted and/or surrounded by the surgical guide.

In some embodiments, the surgical guide includes one or more stop (e.g. mechanical stop) on one or more channel (e.g. drill guide channel, anchoring pin) potentially controlling a maximum drill depth and/or implant insertion depth and/or anchoring pin insertion depth.

In some embodiments, an angle of a drill guide channel is adjustable e.g. with respect to the surgical guide and, in some embodiments, includes one or more lock (e.g. a screw) to lock the drill guide channel in position after adjustment.

FIGS. 16A-B are simplified schematic cross sectional views of a drill guide 1602 within a channel 1608 of a surgical guide 1602, according to some embodiments of the present disclosure. Where, in some embodiments, channel 1608 extends through guide 1606 to underlying patient tissue 1600.

In some embodiments, a drill guide 1602 includes a portion with a rounded shape e.g. a rounded base which, in some embodiments, is held in position in an orientation, by friction (e.g. closely fits) channel 1604 within the surgical guide. In some embodiments, the friction fit is sufficiently robust that a tool is required to apply sufficient force to change the orientation of drill guide 1602 with respect to channel 1608 e.g. as illustrated in the change between FIG. 16A and FIG. 16B.

Exemplary System

Figure 5:
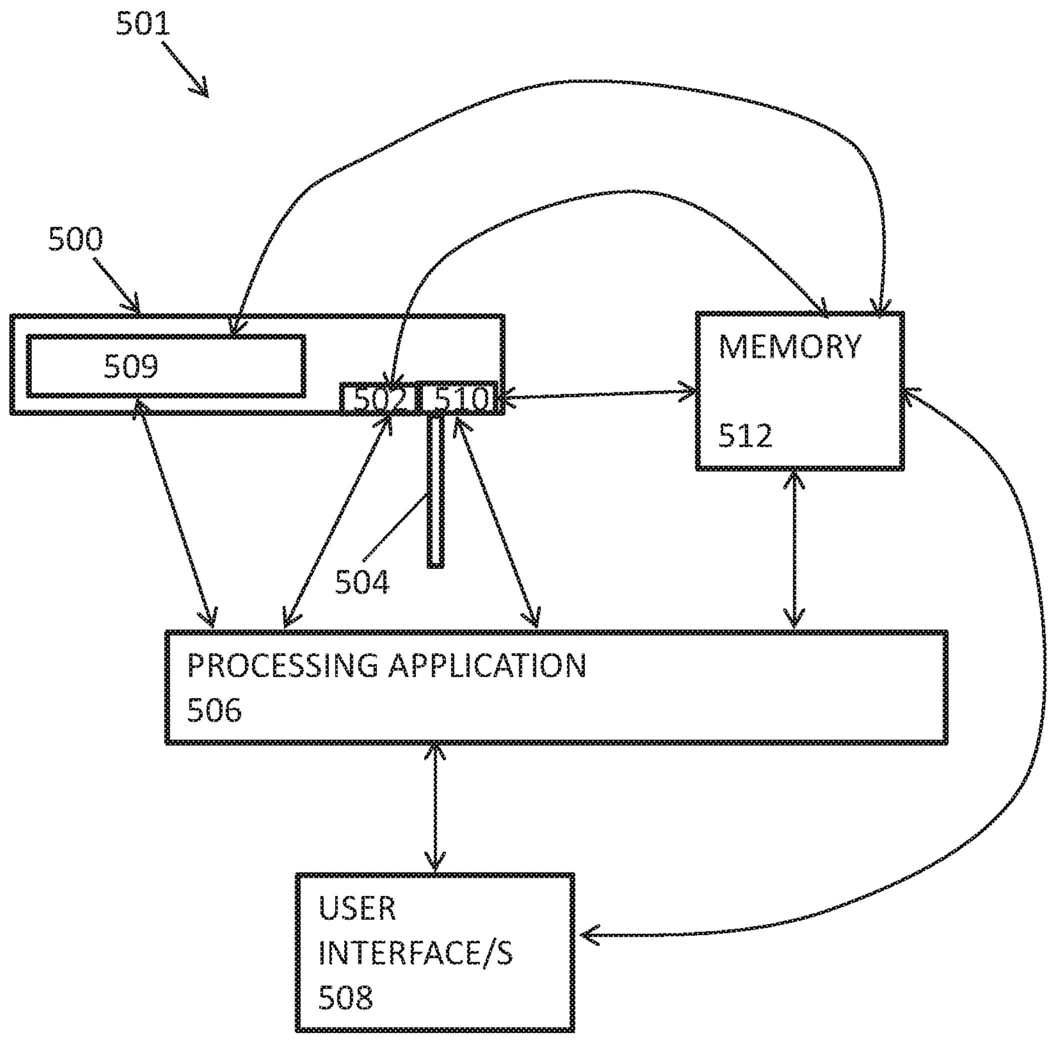
FIG. 5 is a simplified schematic of a system 501 for dental implant guide verification, according to some embodiments of the present disclosure.

FIG. 5 is a simplified schematic of a system 501 for dental implant guide verification, according to some embodiments of the present disclosure.

In some embodiments, a processing application 506 receives signals from imager/s 502 and/or contact sensor/s 510 and/or a memory 512 and/or user interface 508, 509.

In some embodiments, imager/s 502 provide images of a stylus 504 (e.g. of a dental measurement device 500) and/or image guide e.g. as described regarding step 302 FIG. 3 and/or steps 202, 204 FIG. 2.

Figure 6:
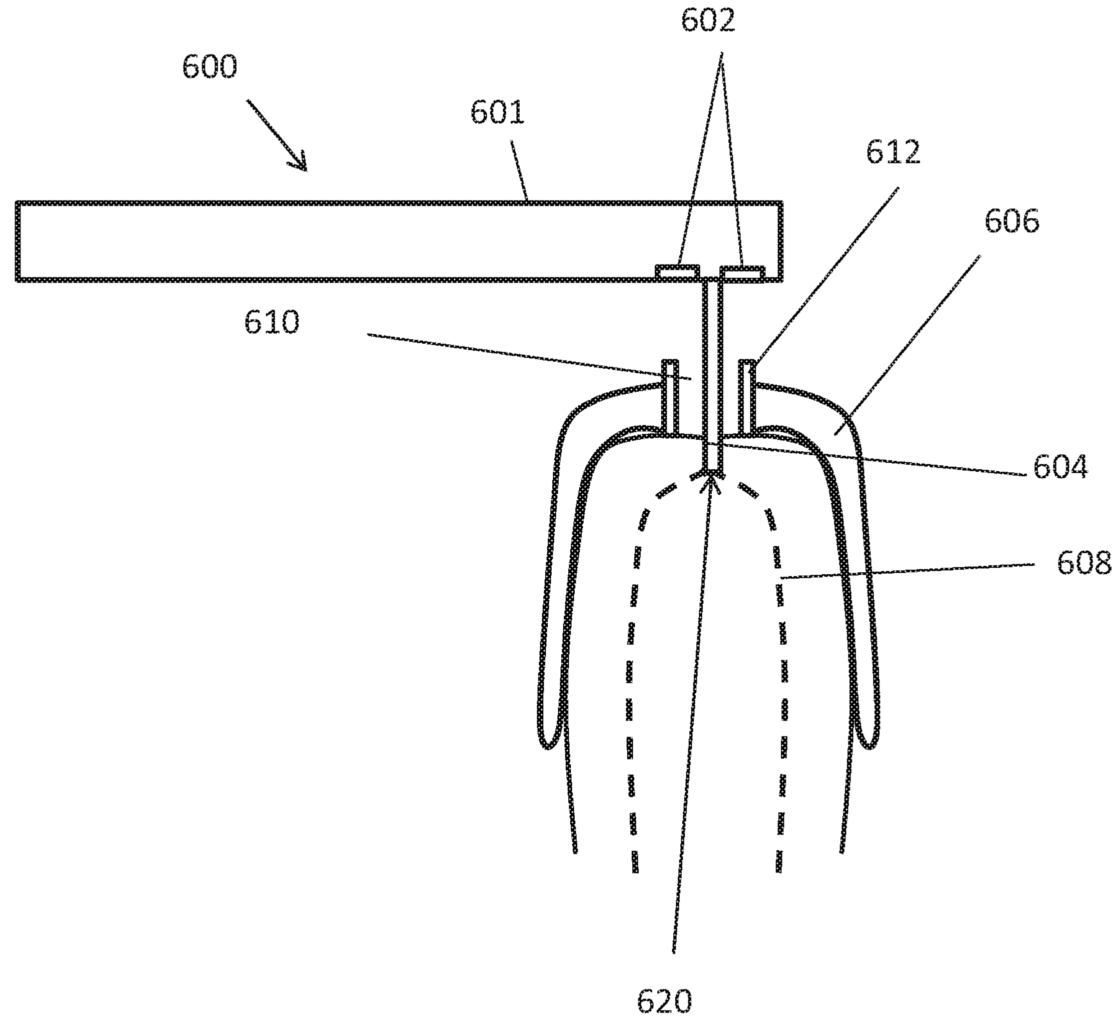
FIG. 6 is a simplified schematic cross-sectional view of a stylus contacting a bone surface through a surgical guide, according to some embodiments of the present disclosure.

In some embodiments, imager/s 502 are part of dental measurement device 500 (e.g. imager/s 602 FIG. 6). Alternatively or additionally, imager/s 502 include imager/s external to and/or not coupled to a stylus of a dental measurement device (not illustrated in FIG. 5).

Optionally, in some embodiments, contact sensor/s 510 provide sensor data regarding contact between stylus 504 (e.g. stylus 604 FIG. 6) and patient bone tissue.

In some embodiments, one or more user interface 509 is part of the dental measurement device. Alternatively or additionally, in some embodiments, the processing application is connected to user interface/s 508 external to the dental measurement device e.g. user interface/s of a control console.

In some embodiments, feedback and/or instructions are communicated to a user through user interface/s 508 and/or 509. For example, in some embodiments, in some embodiments, a user interface indicates to a user instructions regarding measurements to be collected and/or treatment steps. For example, an order of channels to be measured. For example, ordering of drilling.

In some embodiments, the system includes one or more memory 512. In some embodiments, memory 512 provides processing application 506 with model/s of patient mouth structure/s and/or of the surgical guide e.g. including one or more feature as described regarding step 300, FIG. 3. In some embodiments, processing application 506 receives the model/s from implant surgical planning software and/or surgical guide design software.

In some embodiments, memory 512 is used to store measurement data e.g. directly received from imager/s 502 and/or contact sensor/s 510 and/or user interface/s 508 and/or received from processing application 506.

In some embodiments, processing application 506 performs one or more step as described regarding FIG. 3.

In some embodiments, processing application 506 communicates feedback signal/s to a user by sending the signal/s to one or more user interface 508, 509.

Exemplary Measurement, Exemplary Dental Measurement Devices

FIG. 6 is a simplified schematic cross-sectional view of a stylus 604 contacting a bone surface 608 through a surgical guide 606, according to some embodiments of the present disclosure.

In some embodiments, stylus 604 is coupled to and/or is part of a dental measurement device 600. In some embodiments, the dental measurement device 600 includes one or more imager 602. Where, in some embodiments, FOV/s of the imager/s 602 include at least a portion of stylus 610.

In some embodiments, at least a distal portion of dental measurement device 600 including stylus and imager/s 602 is sized and/or shaped for insertion into a human mouth.

In some embodiments, the stylus is detachable from the dental measurement device where, in some embodiments, the stylus is disposable and/or autoclave-able and, in some embodiments, a body 601 of the dental measurement device is re-usable. In some embodiments, dental measurement device 600 is a single use device, being disposed of after a patient treatment session is completed.

In some embodiments, the stylus is detachable from the dental measurement device, for example, potentially enabling use of a styluses with different features e.g. geometry, e.g. sensor/s. In some embodiments, a dental measurement device is provided as a kit with a plurality of styluses e.g. of different type. In some embodiments, e.g. based on model/s and/or inputted information to a processing application (e.g. processing application 506 FIG. 5) the processing application selects a stylus type, for example, communicating the stylus type to be used to a user through a user interface (e.g. user interface/s 508 FIG. 5)

In some embodiments, surgical guide 606 includes one or more drill guide 612 for drilling into bone 608 e.g. as preparation for a dental implant. Where, in some embodiments, stylus 604 is contacted to bone 608 through drill guide 612.

In some embodiments a tip 620 of the stylus is sharp (e.g. as illustrated in FIGS. 9A-C and FIG. 10A), for example, in some embodiments, the stylus is a needle, potentially easing insertion of the stylus through patient soft tissue (e.g. gingiva). In some embodiments, one or more long edge of the stylus includes sharp portion/s, potentially easing lateral movement (e.g. during scanning of the stylus tip along hard surface/s e.g. bone) through soft tissue (e.g. gingiva). In some embodiments, tip 602 is sufficiently blunt and/or includes a stopper (e.g. tip includes a portion with wider cross-section than a cross-section body of the stylus e.g. adjacent to the tip) potentially preventing breach of bone by the stylus tip.

Figures 7A, 7B, 7C:
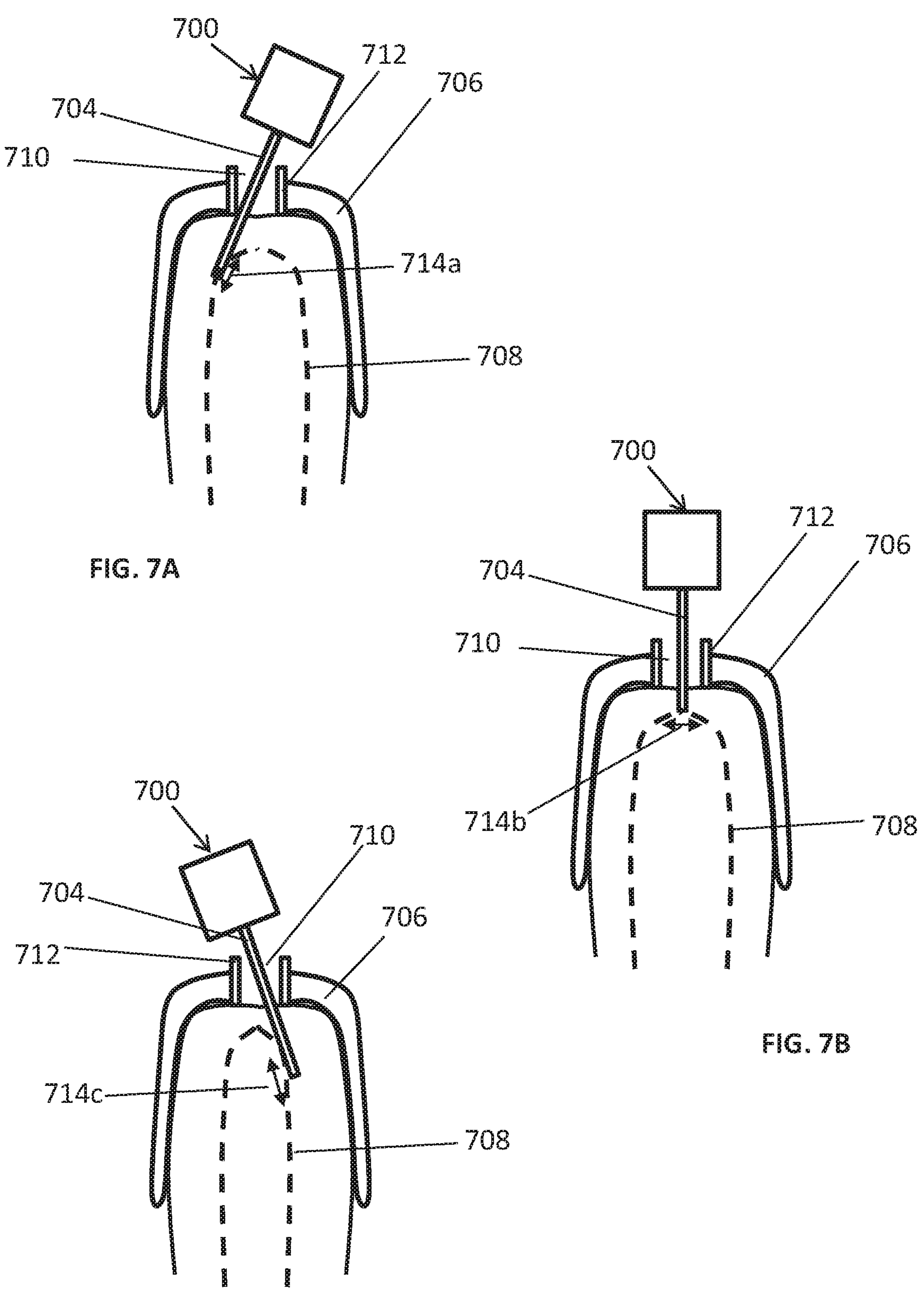
FIGS. 7A-C are simplified schematic cross-sectional views of a stylus contacting a bone surface through a surgical guide, according to some embodiments of the present disclosure.

FIGS. 7A-C are simplified schematic cross-sectional views of a stylus 704 contacting a bone surface 708 through a surgical guide 706, according to some embodiments of the present disclosure.

In some embodiments stylus 704 (e.g. a tip of the stylus) is contacted to a plurality of points on jaw bone 708. For example, as illustrated by different contact points of stylus 704 with bone 708 in FIGS. 7A-C. For example, where an area including a plurality of contact points is illustrated by arrows 714*a*, 714*b*, 714*c* in FIGS. 7A-C.

In some embodiments, the stylus (e.g. the tip of the stylus) is scanned over a portion of bone (e.g. contacted and moved whilst maintaining contact) e.g. as illustrated by arrows 714*a*, 714*b*, 714*c* in FIGS. 7A-C. Where, in some embodiments, stylus is sufficiently rigid and/or sharp (e.g. long edge/s of the stylus are sharp) to be moved through gingiva during scanning.

In some embodiments, measurement is collected of a portion of bone proximal to a drill guide channel 710 e.g. a ridge of a jaw bone e.g. as illustrated in FIG. 7B.

Alternatively or additionally, portion/s of bone adjacent to bone proximal to a drill guide channel are measured, e.g. as illustrated in FIG. 7A and FIG. 7C.

In some embodiments, a stylus of a dental measurement device includes a rounded and/or curved tip.

Figure 8:
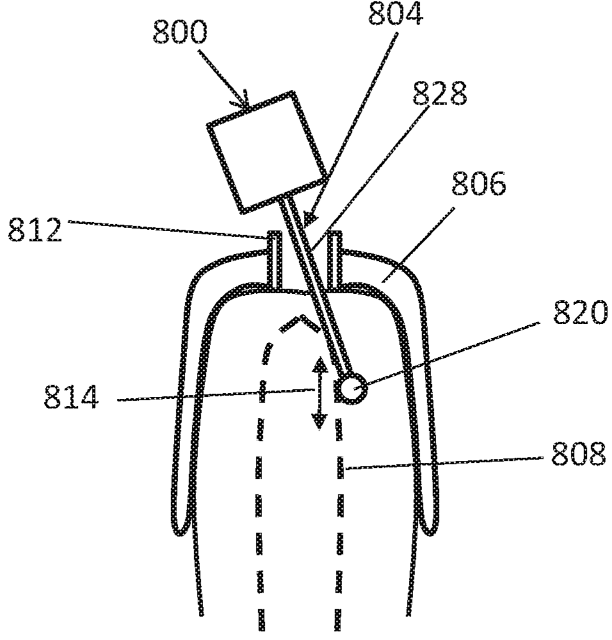
FIG. 8 is a simplified schematic cross-sectional view of a stylus including a spherical tip contacting a bone surface through a surgical guide, according to some embodiments of the present disclosure.

FIG. 8 is a simplified schematic cross-sectional view of a stylus 804 including a spherical tip 820 contacting a bone surface 808 through a surgical guide 806, according to some embodiments of the present disclosure.

Potentially, a spherical tip 820 increases accuracy of measured location of a contact point between the tip and bone surface 808. In some embodiments, spherical tip 820 is configured to roll with respect to a body 828 of stylus 810.

FIG. 9A is a simplified schematic cross-sectional view of a stylus 904 contacting a bone surface through a stylus channel 924 in a surgical guide 906, according to some embodiments of the present disclosure.

FIG. 9B. is a simplified schematic cross-sectional view of a stylus 904 contacting a bone surface through a stylus channel 925 in a surgical guide 906, according to some embodiments of the present disclosure.

FIG. 9C is a simplified schematic cross-sectional view of a stylus 904 contacting a bone surface through a stylus channel 927 in a surgical guide 906, according to some embodiments of the present disclosure.

Referring now to FIGS. 9A and 9C, in some embodiments, a surgical guide 906 includes one or more channel 924, 927 sized and/or shaped to guide stylus 904 to accurately contact a small region of bone surface 908 e.g. the region having size of less than 1 $mm^2$, less than 0.5 $mm^2$, less than 0.1 $mm^2$. In some embodiments, one or more dimensions of the channel e.g. a cross-sectional dimension and/or cross-sectional area of the channel are sized to closely fit the stylus and/or sized and shaped to conform to and receive the stylus. For example, in some embodiments, an average and/or minimum cross-sectional dimension (and/or area) of the channel deviates from a maximum cross-sectional dimension (and/or area) of a portion of the stylus to be inserted into the channel by at most 50%, or 20%, or 10%, or 5%, or 1%.

Alternatively or additionally, referring now to FIG. 9B, in some embodiments, a surgical guide includes one or more channel 925 which has a larger cross-sectional dimension than that of the stylus. For example, potentially enabling several measurements of different contact points with bone 908 to be measured through a single channel. In some embodiments, a cross-sectional area of channel 925 is 1.1-100 times or 2-20 times or 2-10 times or lower or higher ranges or multiples, larger than a cross-section of stylus 904.

In some embodiments, one or more measurement channel 925, 927 is positioned at a position on a surgical guide selected for comfort and/or ease of collection of measurements using the stylus, by the clinician.

Figure 10A:
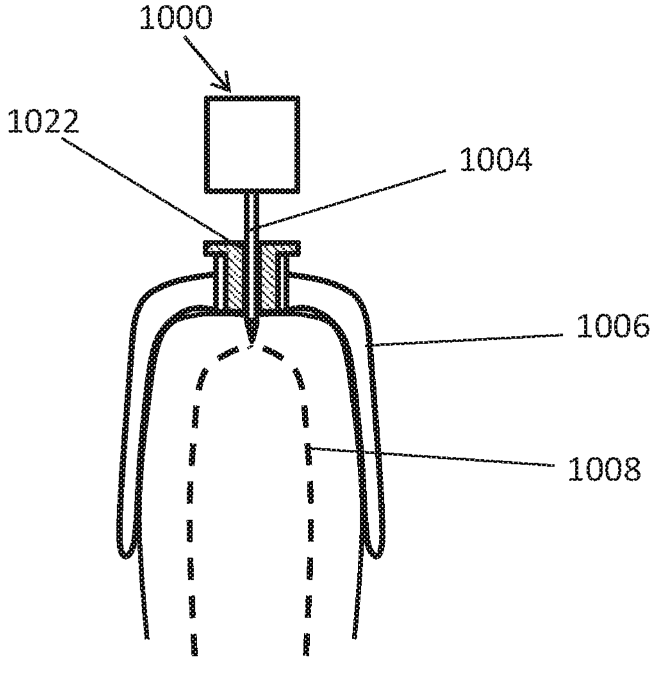
FIG. 10A is a simplified schematic cross-sectional view of a stylus contacting a bone surface through a surgical guide channel insert, according to some embodiments of the present disclosure.

FIG. 10A is a simplified schematic cross-sectional view of a stylus 1004 contacting a bone surface 1008 through a surgical guide channel insert 1022, according to some embodiments of the present disclosure.

In some embodiments, one or more element is used to accurately direct stylus 1004 to a small region of bone surface 1008. For example, one or more element which is configured to be coupled to the surgical guide.

Figure 10B:
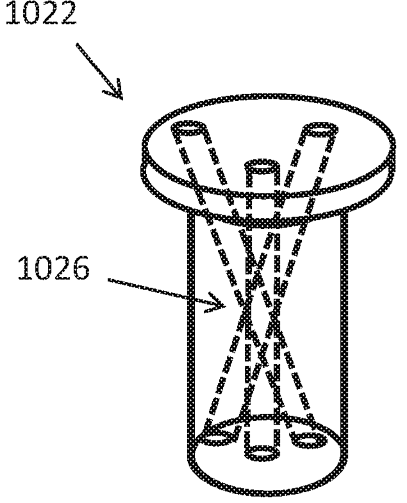
FIG. 10B is a simplified schematic of a surgical guide channel insert, according to some embodiments of the present disclosure.

FIG. 10B is a simplified schematic of a surgical guide channel insert 1022, according to some embodiments of the present disclosure.

In some embodiments, insert 1022 is sized and/or shaped to fit within a channel (e.g. a drill guide channel) of a surgical guide 1006.

In some embodiments, insert 1022 includes one or more channel 1026 through which the stylus is inserted to contact bone 1008. For example, 1-10 channels, or 1-5 channels, or 2, or 3, or 4 channels, or lower or higher or intermediate ranges or numbers of channels.

In some embodiments, one or more channel 1026 is orientated parallel to an axis (e.g. drill axis e.g. long axis) of the channel through the surgical guide (e.g. drill guide). In some embodiments, one or more channel 1026 is orientated at an angle to an axis (e.g. drill axis e.g. long axis) of the channel through the surgical guide.

Exemplary Embodiments of Surgical Guides

Figure 11A:
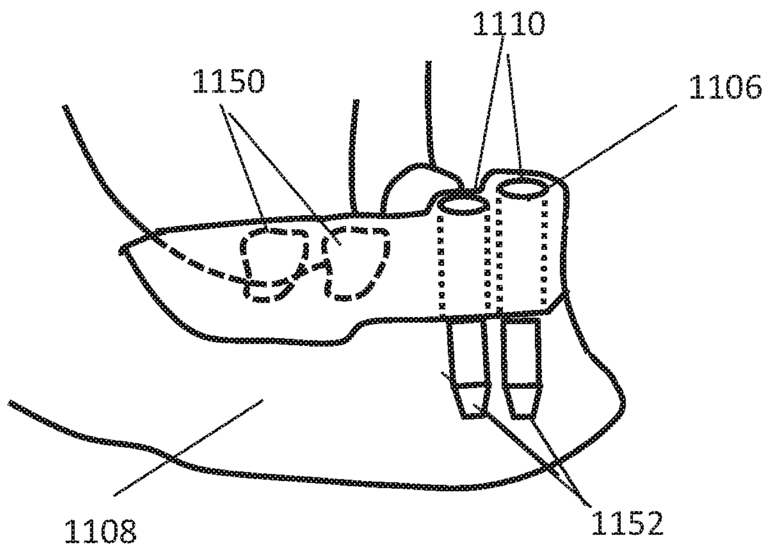
FIG. 11A is a simplified schematic of a surgical guide, according to some embodiments of the present disclosure.

FIG. 11A is a simplified schematic of a surgical guide 1106, according to some embodiments of the present disclosure.

Figure 11B:
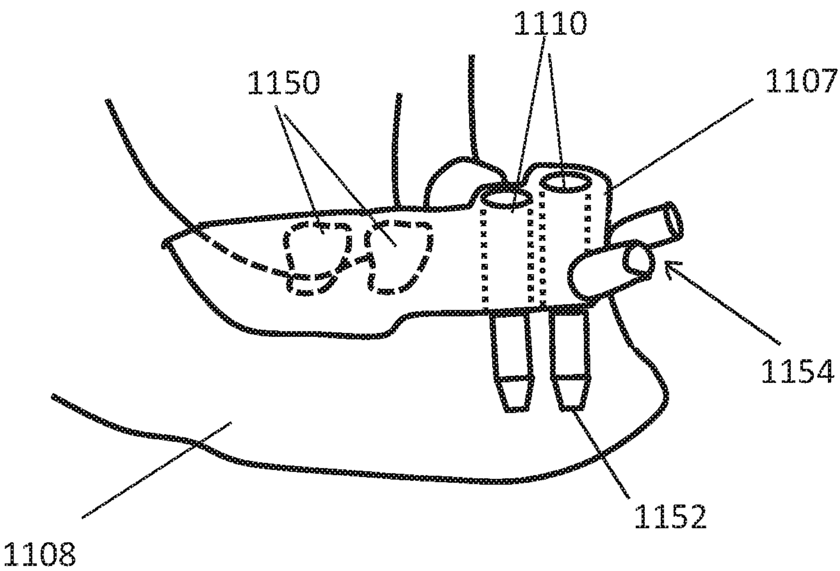
FIG. 11B is a simplified schematic of a surgical guide, according to some embodiments of the present disclosure.

FIG. 11B is a simplified schematic of a surgical guide 1107 including anchoring pin channels 1154, according to some embodiments of the present disclosure.

In some embodiments, FIGS. 11A-B show surgical guides 1106, 1107 positioned with respect to patient bone structure 1108 and/or other hard patient surface/s e.g. teeth 1150. In some embodiments surgical guides 1106, 1107 include drill guides 1110. Elements 1152, in some embodiments, illustrate drill channels within bone structure 1108 and/or implants in situ within bone structure 1108 e.g. drill channels and/or implant position as defined by surgical guides 1106,1107 drill guides 1110.

In some embodiments, a surgical guide, for example, for edentulous jaws, includes one or more anchoring pin channels. In some embodiments, anchoring pin channels 1154 are located at one or more side of the surgical guide, enabling fixing of the surgical guide to underlying bone by anchoring pin/s which contact and/or connect to patient bone. In some embodiments, anchoring pin channels are verified e.g. including one or more technique as described, in this document, regarding verification of drill guide channels.

Figure 12A:
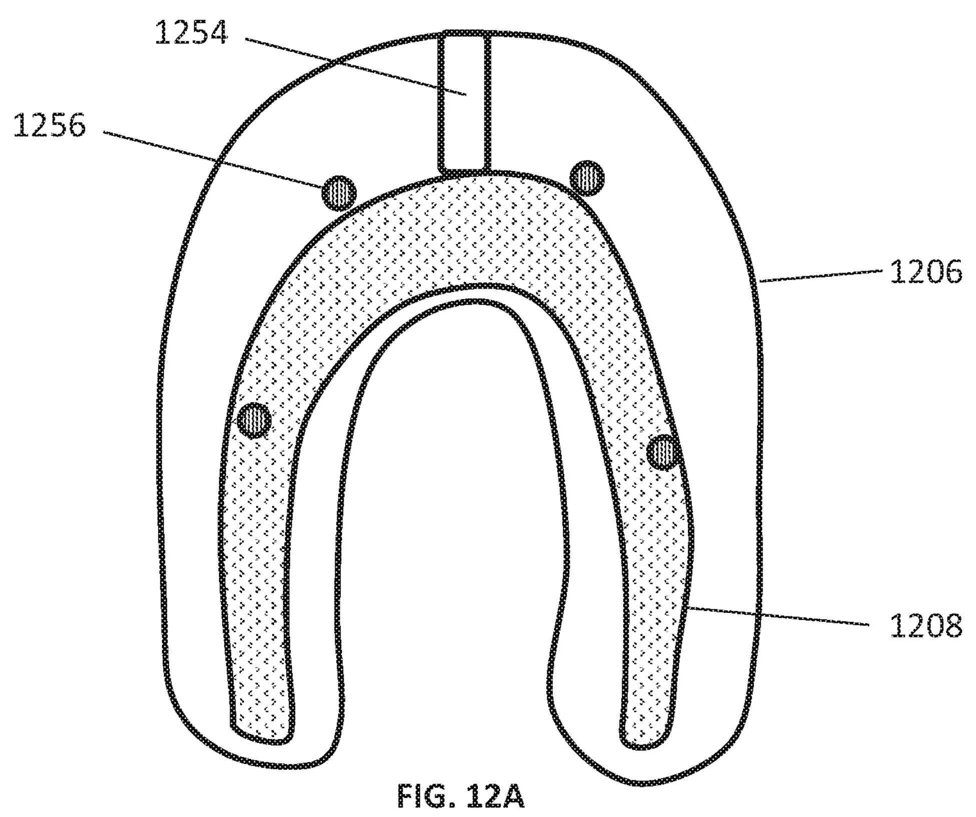
FIGS. 12A-B are simplified schematic top views of a surgical guide in position over a patient jaw, according to some embodiments of the present disclosure.
Figure 12B:
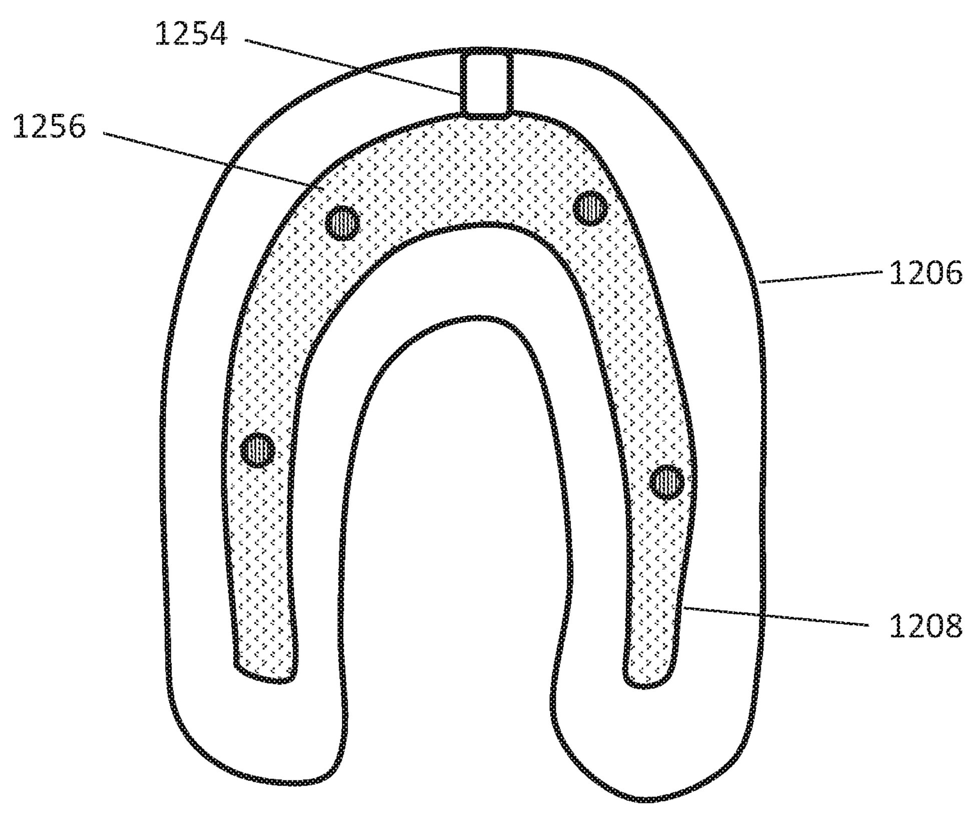

FIGS. 12A-B are top views of a surgical guide 1206 in position over a patient jaw 1208, according to some embodiments of the present disclosure.

In some embodiments, position of surgical guide 1206, with respect to patient structure/s 1208 is adjustable. In some embodiments, the surgical guide 1206 includes an adjustor 1254 where one or more dimension of adjustor 1254 is adjustable e.g. to change a space (and/or to secure the surgical guide to the patient at a different position) between surgical guide 1206 and patient structures 1208. For example, as illustrated by the change in dimension of adjustor 1254 between FIG. 12A and FIG. 12B. Where the surgical guide has moved with respect to the patient structures. The change in position illustrated in FIGS. 12A-B, in some embodiments, shows drill channels 1256 moving from being non-aligned with patient structures 1208 (in FIG. 12A) to being aligned (in FIG. 12B).

In some embodiments, an adjustor includes an anchoring pin where the pin contacts and/or breaches patient bone and where the anchoring pin is adjustable by a user from an outer surface of the surgical guide. For example, by screwing the anchoring pin.

Figure 13A:
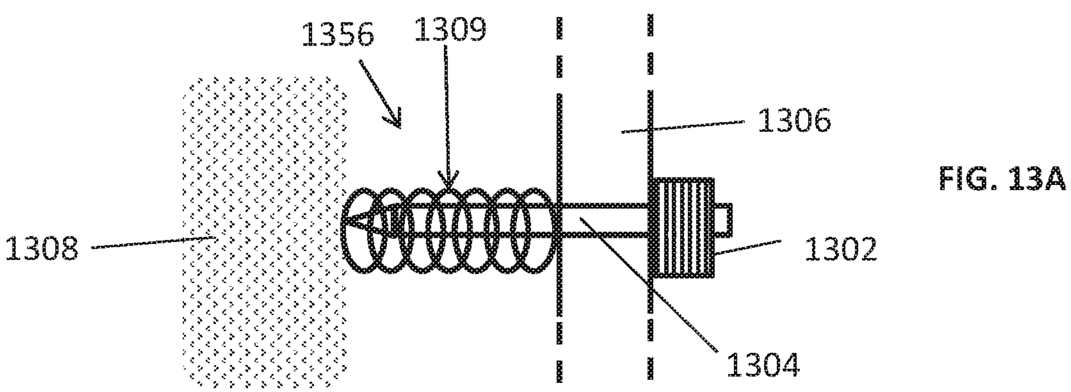
FIGS. 13A-B are simplified schematic views of a portion of a surgical guide including an adjustor, according to some embodiments of the present disclosure.
Figure 13B:
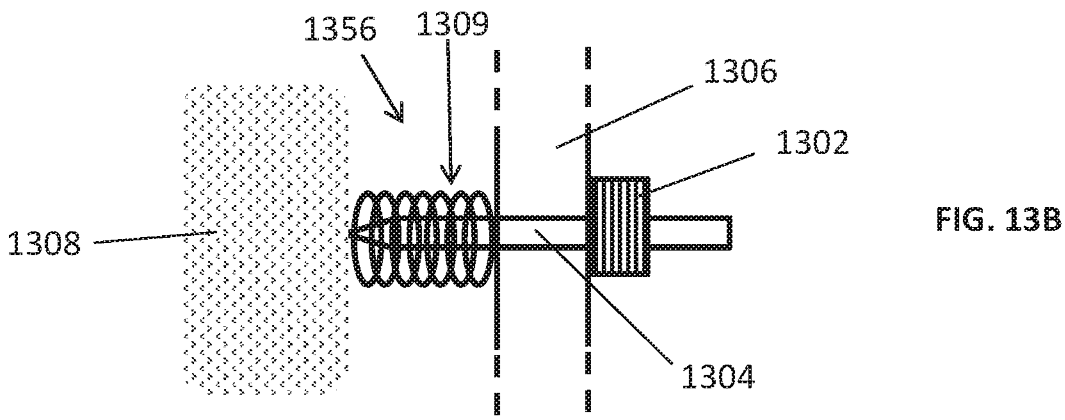

FIGS. 13A-B are simplified schematic views of a portion of a surgical guide 1306 including an adjustor 1356, according to some embodiments of the present disclosure.

In some embodiments, adjustor 1300 is biased towards an expanded configuration, as illustrated by FIGS. 13A-B including a biasing element 1309 (e.g. a spring) (or collapsed configuration).

In some embodiments, a single adjustor includes a control e.g. controls 1302. In some embodiments, an adjustor includes an anchoring pin 1304. In some embodiments, control 1302 controls a separation between a tip of anchoring pin and surgical guide 1306. In an exemplary embodiment, anchoring pin is double threaded, where control 1302 includes a threading. In some embodiments, anchoring pin is adjusted using a hexagon screw e.g. the same hexagon screw which is used to attach implants.

FIGS. 13A-B, in some embodiments, show a change is separation between a patient hard structure 1308 (e.g. patient bone) and surgical guide 1306, e.g. as defined by adjustor 1356.

In some embodiments, an adjustor includes a lock, for example, to lock an adjusted position. In some embodiments, adjustor/s are locked after validation and/or before drilling is commenced.

In some embodiments, feedback provided to a user regarding validation indicates change/s to adjustor/s e.g. a number of revolutions of a screw mechanism of the adjustor. For example, in some embodiments, a dedicated adjustment tool is controlled (e.g. electric screwdriver) e.g. using feedback generated from collected measurements.

In some embodiments, a surgical guide includes more than one adjustor.

Figure 14:
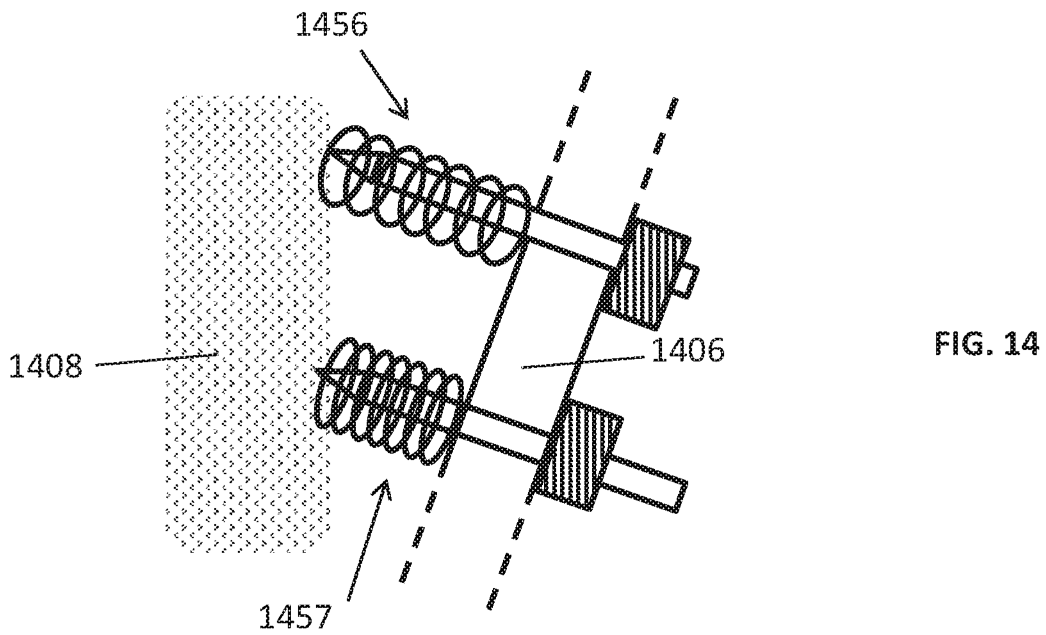
FIG. 14 is a simplified schematic view of a portion of a surgical guide including adjustors, according to some embodiments of the present disclosure.

FIG. 14 is a simplified schematic view of a portion of a surgical guide 1406 including adjustors 1456, 1457, according to some embodiments of the present disclosure. FIG. 14, in some embodiments, illustrates that additional adjustors, in some embodiments, increase a number of degrees of freedom (DOF) of adjustment.

FIG. 15 is a simplified schematic of an adjustable surgical guide 1506, according to some embodiments of the present disclosure.

In some embodiments, an adjustable surgical guide includes multiple portions which are connected by adjustors. For example, as illustrated in FIG. 15, in some embodiments, surgical guide 1506 includes two portions 1562 connected by an adjustor 1506. In some embodiments, the surgical guide includes 3 or 4 or 5 or 2-20, or 2-10, or lower or higher or intermediate portions which are connected by adjustors. In some embodiments, a single adjustor connects more than 2 portions, e.g. 3 parts e.g. 1-10 parts.

In some embodiments, adjustment of adjustor/s 1506 changes a geometry of surgical guide 1506 and/or position of drill channels 1556 on the guide and/or with respect to patient structure/s.

In some embodiments, adjustor/s 1506 are flexible portion/s, e.g. which are elastically and/or plastically deformed by a user to adjust the surgical guide. In some embodiments, adjustor/s 1506 are mechanically adjustable e.g. including one or more screw and/or clamp and/or ratchet and/or one or more feature as described regarding adjustor/s 1254 in FIGS. 12A-B, 1356 in FIGS. 13A-B, 1456 in FIG. 14.

General

It is expected that during the life of a patent maturing from this application many relevant dental implant and/or surgical guide technologies will be developed and the scope of the terms dental implant and/or surgical guide is intended to include all such new technologies a priori.

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this present disclosure may be presented in a range format. It should be understood that the description in range format is merely for convenience and brevity and should not be construed as an inflexible limitation on the scope of the present disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of various inventions disclosed herein, which are, for clarity, described in the context of separate embodiments, may also be provided in combination in a single embodiment (and/or invention). Conversely, various features of the various embodiments/inventions, which are, for brevity, described in the context of a single embodiment, may also be provided separately or in any suitable subcombination or as suitable in any other described embodiment/invention. Certain features described in the context of various embodiments are not to be considered essential features of those embodiments, unless the embodiment is inoperative without those elements.

Although the disclosure, and the various described inventions, have been described in conjunction with specific (example) embodiments, it is evident that many alternatives, modifications and variations will be apparent to those skilled in the art. Accordingly, it is intended to embrace all such alternatives, modifications and variations that fall within the spirit and broad scope of the appended claims. Moreover, some embodiments of the present disclosure may be distinguishable from the prior art by specifically lacking one and/or another structure, feature, step, and functionality not present in the prior art (i.e., claims directed to such embodiments may include one or more negative limitations).

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to any invention/embodiment of the present disclosure. To the extent that section headings are used, they should not be construed as necessarily limiting.

In addition, any priority document(s) of this application is/are hereby incorporated herein by reference in its/their entirety.

What is claimed is:

1. An in-vivo dental surgical guide verification method using a dental measuring device, said dental measuring device comprising a stylus and an imager connected to said stylus, the method comprising:

a. receiving first information comprising:
   i. dental surgical guide information of a dental surgical guide;
   ii. subgingival bone information of a subgingival bone of a patient's mouth; and
   iii. a relation between parts of said dental surgical guide and said subgingival bone when said dental surgical guide is within said patient's mouth;
b. calibrating said imager to said stylus in order to generate a known position of a tip of said stylus in relation to said imager;
c. positioning said surgical guide within said patient's mouth;
d. while said surgical guide within said patient's mouth, contacting said stylus with a surface of said subgingival bone of said patient's mouth;
e. while performing said contacting, acquiring image information corresponding to an image which includes at least a portion of said stylus and a portion of said dental surgical guide therein using said imager;

and f. comparing said image information with said first information, said comparing comprising:
   iv. estimating, using said image information, a first dimension between said dental surgical guide and said patient's mouth subgingival bone in relation to said known position of said tip of said stylus in relation to said imager when performing said contacting;

and v. comparing said first dimension with said first information,
g. detecting if a result of said comparing is a match between said first dimension and said first information thereby verifying that a topography of a preplanned drilling site matches a drilling plan as defined by said dental surgical guide and said expected topography matches the contacted surface of said subgingival bone.

2. The method according to claim 1, wherein said contacting comprises sensing contact between said stylus and said subgingival bone.

3. The method according to claim 1, wherein:

said positioning comprises positioning said dental surgical guide in a position within said patient's mouth;

said subgingival bone information comprises a model of said subgingival bone;

and said method further comprises estimating projected implant position with respect to said subgingival bone, for said position, using said image and said model.

4. The method according to claim 1, wherein said comparing further comprises verifying one or more of:

position of said dental surgical guide within said patient's mouth;

and one or more dimension of said dental surgical guide.

5. The method according to claim 1, including generating feedback based on the comparison.

6. The method according to claim 5, further comprising:

repositioning said dental surgical guide, within said patient's mouth, based on said feedback;

and repeating said contacting, said acquiring and said comparing.

7. The method according to claim 6, wherein said repositioning comprises adjusting at least one adjustor of said dental surgical guide.

8. The method according to claim 5, further comprising:

adjusting a geometry of at least one portion of said dental surgical guide, based on said feedback;

and repeating said contacting, said acquiring and said comparing.

9. The method according to claim 1, wherein said first information further includes one or more of:

a design model of said dental surgical guide;

information corresponding to a virtual design model of said dental surgical guide;

and dimensions of said dental surgical guide.

10. The method according to claim 1, wherein subgingival bone further includes measurement information of said patient mouth subgingival bone.

11. The method according to claim 10, wherein said measurement information comprises CT measurement information.

12. The method according to claim 1, wherein said first information further includes a design model of said dental surgical guide and of said patient's mouth subgingival bone.

13. The method according to claim 1, wherein said first information further includes dimensions of said dental surgical guide and of said patient mouth subgingival bone.

14. The method according to claim 1, wherein said estimating further comprises:

a second dimension defined between said dental surgical guide and said imager;

and a new first dimension defined using:

said second dimension between said dental surgical guide and said imager and a third dimension between a tip of said stylus and said imager.

15. The method according to claim 1, wherein said contacting comprises inserting said stylus through at least one channel provided within said dental surgical guide.

16. The method according to claim 15, wherein said at least one channel comprises a drill guide.

17. The method according to claim 15, wherein said at least one channel comprises an anchoring pin channel.

18. The method according to claim 15, wherein said at least one channel is sized and shaped to conform to and receive said stylus.

19. The method according to claim 1, further comprising repeating said contacting and said acquiring for a plurality of points on said patient mouth subgingival bone.

20. An in-vivo dental surgical guide verification system comprising:

a. a dental measurement device including a distal portion sized and shaped to be inserted into a human mouth, said distal portion comprising:

i. a stylus;

and ii. at least one imager configured to acquire at least one image when said stylus is in contact with a subgingival bone of a patient's mouth, said image including at least a portion of said stylus and at least a portion of a dental surgical guide positioned within a patient's mouth;

b. circuitry configured to:

iii. receive first information comprising:

A. dental surgical guide information of said dental surgical guide;

B. subgingival bone information of said subgingival bone; and

C. a relation between parts of said dental surgical guide and said subgingival bone when said dental surgical guide is within said patient's mouth;

iv. calibrating said imager to said stylus in order to generate a known position of a tip of said stylus in relation to said imager;

v. while said dental surgical guide within said patient's mouth, receive said at least one image, when said stylus is in contact with said patient's mouth subgingival bone;

and vi. compare said at least one image with said first information by:

D. estimating, using said at least one image, a first dimension between said dental surgical guide and said patient's mouth subgingival bone in relation to said known position of said tip of said stylus in relation to said imager when performing said contacting;

and

E. comparing said first dimension with said first information;

vii. detecting if a result of said comparing is a match between said first dimension and said first information thereby verifying that a topography of a preplanned drilling site matches a drilling plan as defined by said dental surgical guide and said expected topography matches the contacted surface of said subgingival bone.

* * * * *